United States Patent
Kim et al.

(10) Patent No.: US 7,845,938 B2
(45) Date of Patent: Dec. 7, 2010

(54) INDIRECT BONDING TRAYS FOR ORTHODONTIC TREATMENT AND METHODS FOR MAKING THE SAME

(75) Inventors: Sungham Kim, Montebello, CA (US); Calvin N. Corpus, Diamond Bar, CA (US); Ming-Lai Lai, Arcadia, CA (US); David K. Cinader, Jr., Walnut, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 359 days.

(21) Appl. No.: 11/689,845

(22) Filed: Mar. 22, 2007

(65) Prior Publication Data

US 2008/0233528 A1 Sep. 25, 2008

(51) Int. Cl.
*A61C 3/00* (2006.01)
(52) U.S. Cl. .............................. 433/3; 433/9
(58) Field of Classification Search ............ 433/24, 433/29, 3, 8–12, 213–226; 206/63.5
See application file for complete search history.

(56) References Cited

U.S. PATENT DOCUMENTS

| | | | |
|---|---|---|---|
| 3,738,005 A | 6/1973 | Cohen et al. | |
| 3,949,477 A | 4/1976 | Cohen et al. | |
| 4,183,141 A | 1/1980 | Dellinger et al. | |
| 4,360,341 A | 11/1982 | Dellinger | |
| 4,487,580 A | 12/1984 | Ridgeway | |
| 4,501,554 A | 2/1985 | Hickham | |
| 4,551,096 A | 11/1985 | Dellinger | |
| 4,793,803 A * | 12/1988 | Martz .............................. 433/6 |
| 4,822,277 A | 4/1989 | Nevell | |
| 5,015,180 A | 5/1991 | Randklev | |
| 5,172,809 A | 12/1992 | Jacobs et al. | |
| 5,354,199 A | 10/1994 | Jacobs et al. | |
| 5,429,229 A | 7/1995 | Chester et al. | |
| 5,542,842 A | 8/1996 | Andreiko et al. | |
| 5,971,754 A * | 10/1999 | Sondhi et al. .................. 433/24 |
| 6,123,544 A | 9/2000 | Cleary | |
| 6,183,249 B1 | 2/2001 | Brennan et al. | |
| 6,244,861 B1 | 6/2001 | Andreiko et al. | |
| 6,302,688 B1 | 10/2001 | Jordan et al. | |
| 6,331,080 B1 | 12/2001 | Cole et al. | |

(Continued)

FOREIGN PATENT DOCUMENTS

WO    WO 02/089693    11/2002

OTHER PUBLICATIONS

Pending U.S. Appl. No. 11/551,823, filed Oct. 23, 2006.

(Continued)

*Primary Examiner*—Ralph A Lewis
*Assistant Examiner*—Yogesh Patel
(74) *Attorney, Agent, or Firm*—James Christoff; Kevin Weber

(57) ABSTRACT

An indirect bonding tray places orthodontic appliances in precise, predetermined positions on the teeth of a patient. The indirect bonding tray includes a first matrix material that extends over a set of appliances and a second matrix material that extends over the first matrix material. The indirect bonding tray also includes at least one occlusal stop member that is connected to the second matrix material for firm, relatively hard contact with the occlusal tips of the patient's teeth when the tray is received in place over the patient's dental arch.

19 Claims, 11 Drawing Sheets

U.S. PATENT DOCUMENTS

| | | |
|---|---|---|
| 6,444,725 B1 | 9/2002 | Trom et al. |
| 6,528,555 B1 | 3/2003 | Nikutowski et al. |
| 6,554,613 B1 | 4/2003 | Sachdeva et al. |
| 6,670,436 B2 | 12/2003 | Burgath et al. |
| 6,960,079 B2 | 11/2005 | Brennan et al. |
| 7,020,963 B2 | 4/2006 | Cleary et al. |
| 7,137,812 B2 | 11/2006 | Cleary et al. |
| 7,168,950 B2 | 1/2007 | Cinader, Jr. et al. |
| 2004/0219471 A1* | 11/2004 | Cleary et al. ............ 433/3 |
| 2004/0253562 A1 | 12/2004 | Knopp |
| 2005/0074717 A1 | 4/2005 | Cleary et al. |
| 2005/0175965 A1 | 8/2005 | Craig et al. |
| 2005/0175966 A1 | 8/2005 | Falsafi et al. |
| 2005/0176844 A1 | 8/2005 | Aasen et al. |
| 2005/0233276 A1 | 10/2005 | Kopelman et al. |
| 2005/0244790 A1 | 11/2005 | Kuperman |
| 2006/0134580 A1 | 6/2006 | Raby et al. |
| 2006/0177791 A1 | 8/2006 | Cinader, Jr. |
| 2006/0223021 A1 | 10/2006 | Cinader, Jr. et al. |
| 2006/0223031 A1 | 10/2006 | Cinader, Jr. et al. |
| 2006/0257821 A1 | 11/2006 | Cinader et al. |
| 2007/0031774 A1 | 2/2007 | Cinader, Jr. et al. |

OTHER PUBLICATIONS

Pending U.S. Appl. No. 11/422,613, filed Jun. 7, 2006.
Pending U.S. Appl. No. 11/422,614, filed Jun. 7, 2006.
Pending U.S. Appl. No. 11/689,856, filed Mar. 22, 2007.
Pending U.S. Appl. No. 11/689,869, filed Mar. 22, 2007.

* cited by examiner

INDIRECT BONDING TRAYS FOR ORTHODONTIC TREATMENT AND METHODS FOR MAKING THE SAME

BACKGROUND OF THE INVENTION

1. Field of the Invention

This invention relates to trays that are used by orthodontic practitioners to bond appliances to the teeth of an orthodontic patient. The invention is also related to methods for making such bonding trays.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the upper and lower teeth are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In many types of orthodontic techniques, the precise position of the appliances on the teeth is an important factor for helping to ensure that the teeth move to their intended final positions. For example, one common type of orthodontic treatment technique is known as the "straight-wire" technique, where the archwire lies in a horizontal plane at the conclusion of treatment. Consequently, the brackets must be correctly positioned at the beginning of treatment so that the teeth are properly aligned once the archwire straightens and lies in the horizontal plane. If, for example, a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

One technique for bonding orthodontic appliances to teeth is known as an indirect bonding technique. In the past, known indirect bonding techniques have often used a placement device or transfer apparatus having a shape that matches a configuration of at least part of the patient's dental arch. One type of transfer apparatus is often called a "transfer tray" or "indirect bonding tray" and typically has a cavity for simultaneously receiving a number of teeth. A set of appliances such as brackets are releasably connected to the tray at certain, predetermined locations.

During the use of a bonding tray for indirect bonding, an adhesive is typically applied to the base of each appliance by the orthodontist or a staff member. The tray is then placed over the patient's teeth and remains in place until such time as the adhesive hardens. Next, the tray is detached from the teeth as well as from the appliances, with the result that all of the appliances previously connected to the tray are now bonded to respective teeth at their intended, predetermined locations.

Indirect bonding trays are normally custom-made for each patient because the size and orientation of teeth can vary widely from one patient to the next. One method of making indirect bonding trays includes the steps of taking an impression of each of the patient's dental arches and then making a replica plaster or "stone" model from each impression. If desired, the teeth of the model can be marked with a pencil to assist in placing the brackets in ideal positions. Next, the brackets are temporarily bonded to the stone models. An indirect bonding tray is then made by placing matrix material over the model as well as over the brackets on the model. For example, a plastic sheet matrix material may be placed over the model and brackets and then heated in an oven under vacuum. As the plastic sheet material softens and as air in the oven is evacuated, the plastic sheet material assumes a configuration that precisely matches the shape of the replica teeth of the stone model and adjacent brackets. The plastic material is then allowed to cool and harden to form a tray.

While the state of the art with respect to indirect bonding trays has advanced in recent years, there is a continuing need to improve the accuracy of the placement of the appliances on the patient's teeth by such trays. Some orthodontists, for example, can detect very small differences (such as, for example, 0.5 mm) in positions of appliances with the naked eye and consequently may not be satisfied with the use of indirect bonding trays that do not consistently place appliances within such tolerances.

SUMMARY OF THE INVENTION

The present invention is directed toward improved indirect bonding trays for orthodontic treatment as well as methods for making the same. The indirect bonding tray includes a first and second matrix material, as well as at least one occlusal stop member that is connected to the second matrix material. In preferred embodiments of the indirect bonding tray of the invention provides a tactile "snap-fit" that is perceptible by touch when placed over the teeth of the patient and as such provides confirmation that the appliances are brought into desired positions over intended areas of the patient's teeth. The snap-fit relation of the bonding tray to the teeth also helps to reduce the amount, if any, of unintended lateral movement of the tray before such time as the appliances are firmly bonded to the patient's teeth.

In more detail, the present invention in one aspect is directed toward an indirect bonding tray for orthodontic treatment. The indirect bonding tray includes a set of orthodontic appliances and a first matrix material that extends over the appliances. The indirect bonding tray also includes a second matrix material that extends over the first matrix material. The second matrix material includes a portion having a surface with a configuration that matches the configuration of a portion of side (i.e., labial or lingual) tooth surfaces. The indirect bonding tray also includes at least one occlusal stop member connected to the second matrix material, and the occlusal stop member includes a portion having a surface with a configuration that matches at least a portion of occlusal tooth surfaces.

Another aspect of the present invention is directed toward a method of making an indirect bonding tray for orthodontic treatment. The method comprises:

providing an occlusal stop member having a surface with a configuration that matches at least a portion of occlusal surfaces of a patient's dental arch;

placing orthodontic appliances onto tooth surfaces of a model of the patient's dental arch;

placing the stop member on occlusal surfaces of the dental arch model;

applying a quantity of a first matrix material to the orthodontic appliances;

allowing the first matrix material to harden;

placing the dental arch model, the orthodontic appliances and a first matrix material in a vessel;

adding a quantity of a second matrix material to the vessel;

allowing the second matrix material to harden; and removing the dental arch model; the orthodontic appliances, the stop member and the second matrix material from the vessel.

Another aspect of the invention is also directed toward a method of making an indirect bonding tray for orthodontic treatment. This method comprises:

providing a digital data file that is representative of at least a portion of a patient's dental arch;

forming a model of the patient's dental arch, an occlusal stop member and a tray molding vessel by rapid prototyping using the digital data file;

placing orthodontic appliances onto tooth surfaces of the dental arch model;

contacting the stop member with occlusal tooth surfaces of the dental arch model;

adding a quantity of a matrix material to the vessel;

placing the dental arch model and the orthodontic appliances in the vessel; and allowing the matrix material to harden.

These and other aspects of the invention are described in more detail in the paragraphs that follow and are illustrated in the accompanying drawings.

DEFINITIONS

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

DETAILED DESCRIPTION OF THE PREFERRED EMBODIMENTS

Figure 1:
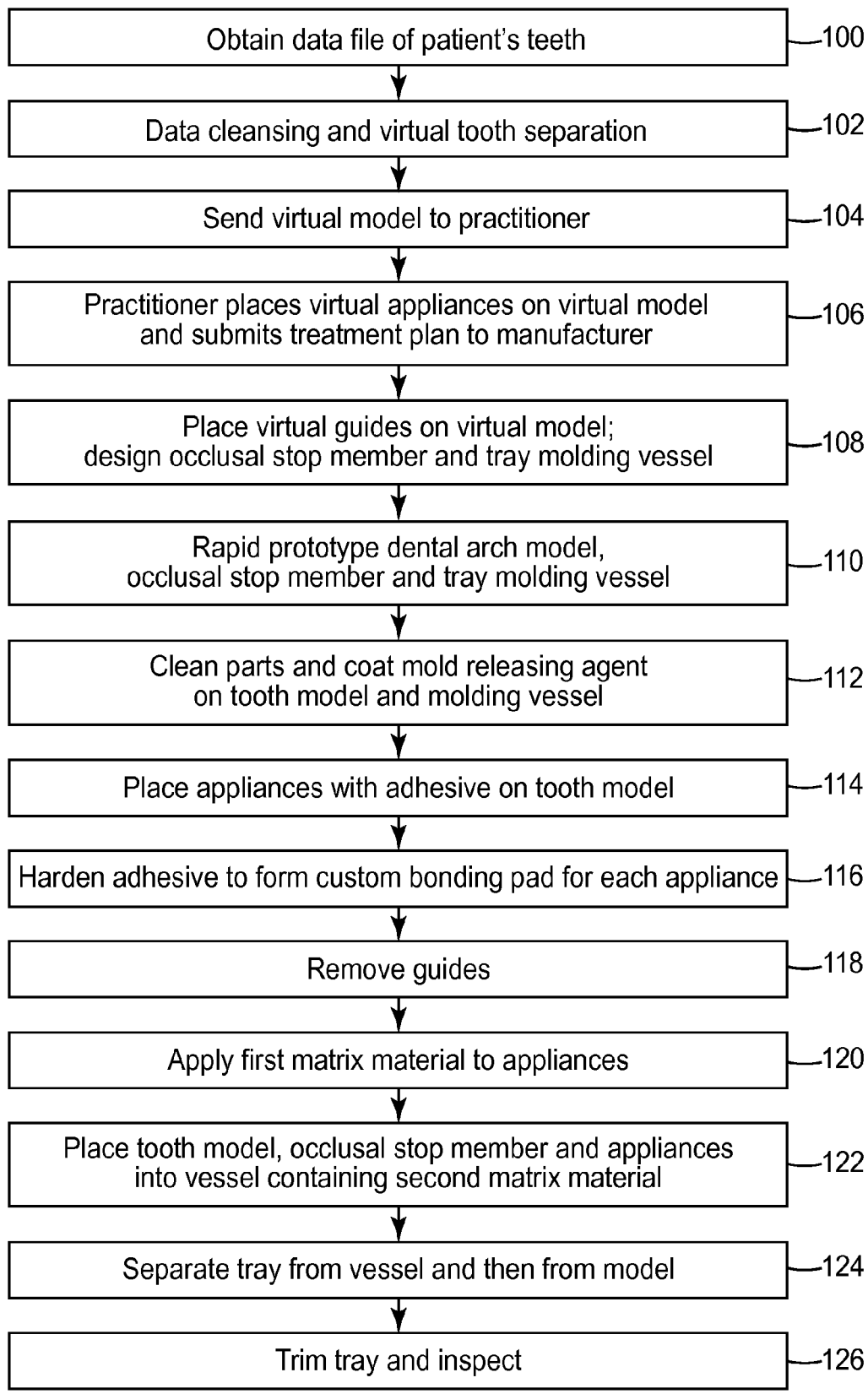
FIG. 1 is a block diagram describing some of the steps that are followed in making an indirect orthodontic bonding tray according to one embodiment of the invention.

FIG. 1 is a block diagram describing some of the steps that are carried out in making an indirect bonding tray for orthodontic treatment according to one embodiment of the present invention. Block 100 represents the step of obtaining a digital data file of the patient's teeth and optionally the patient's adjacent gingival tissue. The digital data may be obtained by the use of a hand-held intra-oral scanner such as the intra-oral scanner using active wavefront sampling developed by Brontes Technologies, Inc. Alternatively, other intra-oral scanners or intra-oral contact probes may be used. As another option, the digital data file may be obtained by scanning an impression of the patient's teeth. As still another option, the digital data may be obtained by scanning the physical model of the patient's teeth or by using a contact probe on the patient's teeth. The model used for scanning may be made by pouring a casting material (such as plaster of Paris or epoxy resin) into an impression of the patient's teeth and allowing the casting material to cure. Any suitable scanning technique may be used for scanning the model, such as X-ray, laser, computed tomography (CT), and magnetic resonance imaging.

In block 102, the digital data file of the patient's teeth obtained in block 100 is "cleansed" by removing any data points that represent clear error. For example, STL files representing a tooth surface that include a data point significantly outside the normal expected geometrical relationship of adjacent data points could be fixed by STL-handling software to remove the erroneous data point. In addition, tooth data points that are missing could be added by STL-handling software to create realistic, smoothly curved tooth shapes. Alternatively, or in addition to, the data cleansing may be carried out on the data file before conversion of the data to an STL file.

As an additional option, data may also be obtained of hidden features of the patient, such as the roots of the patient's teeth and the jaw structure. For example, CT scanning techniques may be used to obtain data representative of the patient's entire tooth structure including the roots. The data obtained by CT scanning may then be "stitched together" with other data obtained by scanning the crowns of the patient's teeth with another scanning technique so that the practitioner may ultimately obtain a better understanding of tooth movement during the course of treatment.

As also represented by block 102, the digital data file of the patient's dental arch is then modified to provide virtual separation of each tooth from adjacent teeth and gingiva so that each tooth may be independently moved as a separate object. Next, and as represented by block 104, the modified virtual model is forwarded to the practitioner. For example, if the steps in block 102 are carried out at a manufacturing facility, the facility may send the virtual model to the practitioner over a wired communications network such as the internet. The practitioner then interacts with a local computer to view the three dimensional ("3D") virtual model and determine the desired final positions of the patient's teeth.

As shown in block 106, the practitioner selects and places virtual appliances such as brackets and buccal tubes on the virtual model using the local computer. During this process, the practitioner selects virtual appliances that embody certain geometric attributes and also selects the positions of the appliances on the patient's teeth within the modeling environment. The modeling software manipulates each bracket and each tooth as a separate object within the 3D environment and fixes the position of each bracket within the 3D space relative to a coordinate system associated with the tooth of the corresponding bracket. The modeling software then computes the final positions of the teeth based on the positions of the appliances selected by the practitioner and displays the virtual teeth in their final occlusion.

If the practitioner is not entirely satisfied with the final predicted positions of the teeth, the practitioner may use the modeling software to move one or more of the virtual appliances relative to the virtual teeth. The modeling software will then compute and display new final positions of the virtual teeth based on the revised positions of the virtual appliances on the virtual teeth. These steps can be repeated as many times as desired until the practitioner is satisfied with the final positions of the virtual teeth as represented by the modeling software. As an alternative to moving appliances, however, the practitioner may use the modeling software to move the virtual teeth to desired positions, and the modeling software will then compute positions of the appliances on the teeth for moving the teeth to those desired positions. Data representing the selected positions of the appliances, along with identification data for each appliance (such as brand name and the manufacturer's part number), tooth identification data (such as tooth type and location in the oral cavity) and patient data (such as name and birth date, or a patient identification number) is then submitted to the manufacturing facility.

Optionally, the local computer at the practitioner's office may include subprograms suitable to analyze the existing malocclusion of the patient and assist in determining the desired ultimate positions of the appliances on the patient's teeth. The software may also include subprograms to assist in suggesting or selecting the proper appliances for treatment of the particular malocclusion at hand.

As yet another option, the steps in block 106 may be carried out by a technician at a location remote from the practitioner's office. For example, a technician at the manufacturer's facility may use software to place virtual appliances on the virtual dental model in accordance with known standards in the art or in accordance with general guidelines previously provided by the practitioner. Once the technician is satisfied with the appliance positions and the resulting finished positions of the teeth, the virtual model together with the data representing the appliance positions is forwarded to the practitioner for review. The practitioner can then either approve the technician's appliance placement positions or reposition the appliances as desired. The practitioner then forwards the virtual model together with the appliance tooth and patient data as mentioned above back to the manufacturer.

Block 108 describes steps that are preferably undertaken at the manufacturer's facility using data of the virtual dental model and identification data of the appliances and position data of the appliances. Alignment structure for use in placing appliances on a physical model are created by first creating one or more virtual guides on the virtual model using software. Preferably, virtual guides are created corresponding to each appliance. In addition, one or more occlusal stop members are designed and the shape of a tray molding vessel is determined. A data file of the virtual model with the guides, a data file of the occlusal stop member and a data file of the tray molding vessel are then forwarded to a rapid prototyping machine as described in block 110. The occlusal stop member and the tray molding vessel are described in more detail below.

As used herein, rapid prototyping is the process of generating an object directly from digital data, such as digital data representing its shape. Examples of suitable rapid prototyping processes include solid freeform fabrication such as 3D printing processes, stereolithography methods, fused deposition modeling, laminated object manufacturing, laser engineered net shaping, selective laser sintering, shape deposition manufacturing and solid ground curing. An example of a suitable 3D printing machine is the Eden brand 500V printer from Objet Geometries Ltd., using FullCure 720 acrylic-based photopolymer printing material (also from Objet Geometries Ltd.). Another example of rapid prototyping is the use of CAD-CAM software to direct a milling machine to mill the dental arch model with the alignment guides, the occlusal stop member and the tray molding vessel. The manufactured parts are then cleaned as described in block 112.

Figure 2:
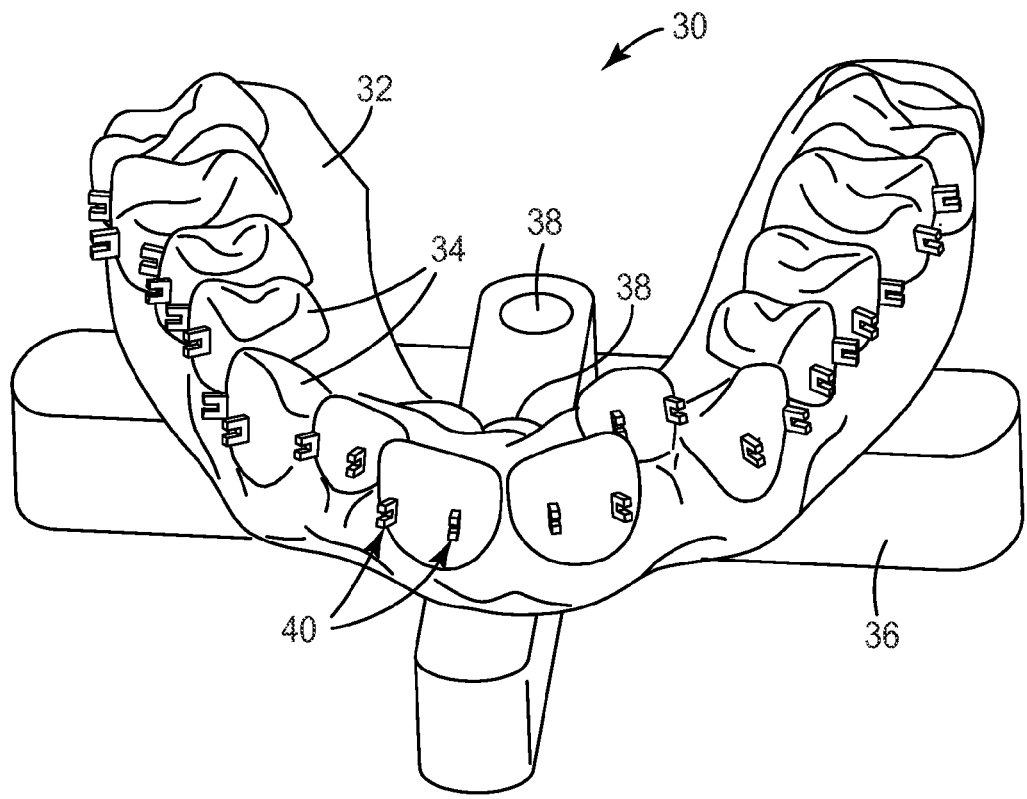
FIG. 2 is a perspective view showing a model of a patient's dental arch as described in FIG. 1, looking in directions toward facial and occlusal surfaces of the arch model and additionally showing a substrate of the arch model.

An exemplary dental arch model 30 made by rapid prototyping is illustrated in FIG. 2. In this embodiment, the arch model 30 includes a portion of the model gingival tissue 32 as well as individual model teeth 34. The arch model 30 as shown represents the patient's entire lower dental arch, and preferably a model of the patient's upper dental arch (not shown) is also provided. Alternatively, the arch model may include only a portion of the arch (for example, an arch quadrant) in instances where the resulting indirect bonding tray is to be used to bond appliances to only a portion of the patient's dental arch. Optionally, when the arch model 30 is made using a 3D printing machine, the arch model 30 could be hollow to reduce the expense associated with the printing material.

In addition to the model gingival tissue 32 and the model teeth 34, the arch model 30 also includes a pedestal or substrate 36. In this embodiment, the substrate 36 has the shape of a cross and includes alignment structure comprising two holes 38, the purpose of which will be explained below. However, the substrate 36 may be constructed in other shapes as well, such as a generally circular-shaped disk that extends along the base of the model gingival tissue 32. Preferably, the arch model is printed as a single, unitary component such that the substrate 36 is integrally connected with the model gingival tissue 32.

The guides as mentioned in block 108 preferably include one or more guides associated with each appliance and its corresponding model tooth 34 for properly positioning the appliance on the model tooth 34. In the embodiment shown in FIGS. 2-5 and 8-10, two guides 40 are integrally connected to each model tooth 34 as a consequence of being fabricated by rapid prototyping during rapid prototyping of the arch model 30. Each of the guides 40 includes a generally U-shaped body 42 (see, e.g., FIGS. 3 and 5) with a channel 44 defined by occlusal, lingual and gingival walls that are optionally flat.

Figure 3:
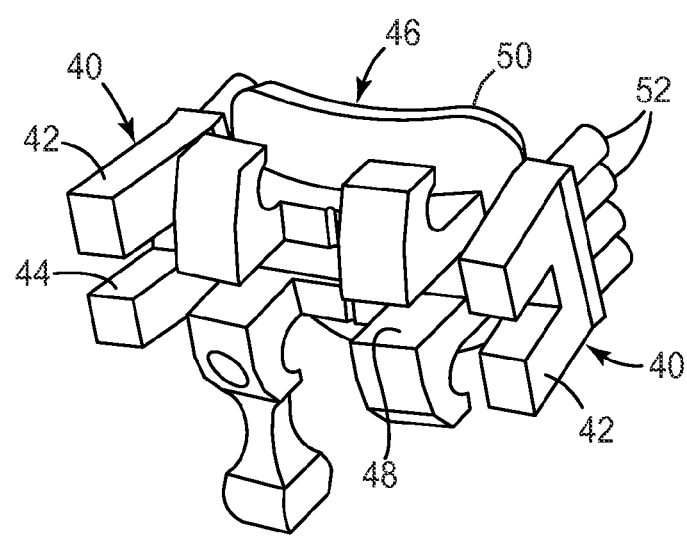
FIG. 3 is an enlarged perspective view showing exemplary alignment guides of the dental arch model illustrated in FIG. 2 along with an exemplary orthodontic appliance in contact with the guides as it might appear when the appliance is placed on the model, and looking in a direction toward the facial and occlusal surfaces of the appliance.
Figure 4:
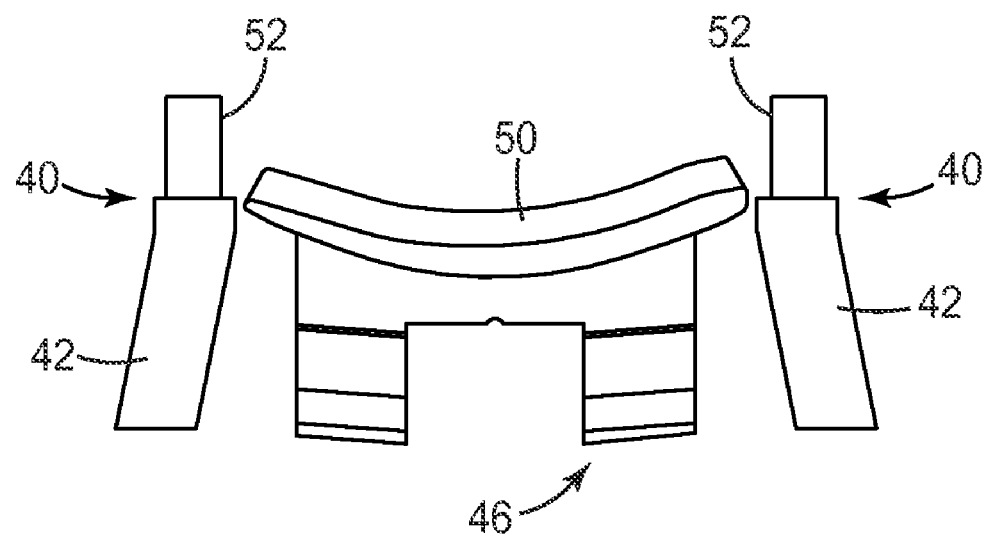
FIG. 4 is a top view of the guides and appliance shown in FIG. 3, looking in a direction toward the occlusal surfaces of the appliance.
Figure 5:
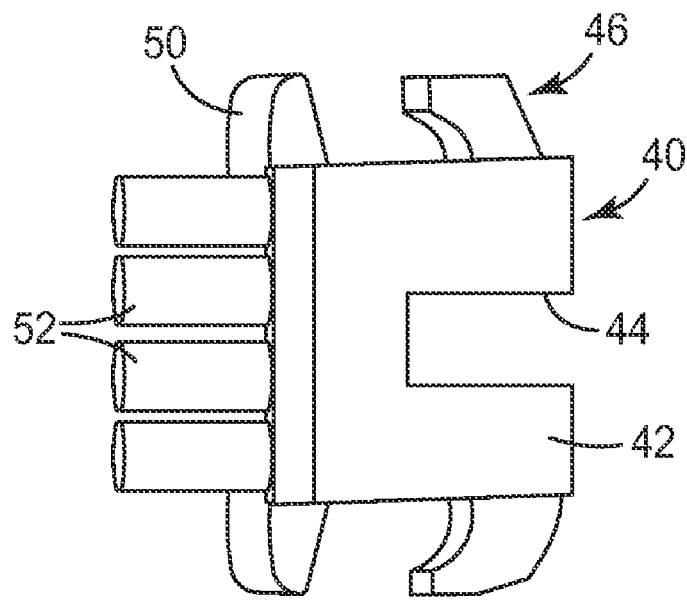
FIG. 5 is a side view of the appliance and guides shown in FIGS. 3 and 4, looking in a direction toward a distal side of the appliance.

An exemplary orthodontic bracket appliance 46 is shown in FIGS. 3-5 and is received in the space between the two guides 40 associated with one of the model teeth 34. The appliance 46 has an archwire slot 48 (FIG. 3) adapted to matingly receive an archwire. In this example, the appliance 46 is known as a twin tiewing bracket and includes a hook. However, other orthodontic appliances having an archwire slot may be used as well.

The guides 40 each have a known physical characteristic relative to the archwire slot 48 of the corresponding appliance 46. In the illustrated embodiment, the known physical characteristic of the guides 40 includes the orientation of the three walls defining the channel 44. For example, and in this embodiment, the occlusal, lingual (or bottom) and gingival walls of the channel 44 of each guide 40 are coplanar with the occlusal, lingual and gingival walls respectively of the archwire slot 48 when the appliance 46 is properly positioned on the model tooth 34 and between the guides 40.

However, alternative constructions are also possible. For example, the three walls of the channel 44 could extend in reference planes that are offset but parallel to the respective three walls defining the archwire slot 48. As yet another example, the three walls of the channel 44 of each guide 40 may be oriented at an angle relative to the respective three walls of the archwire slot 48.

As another alternative construction, the guides could be located along occlusal and gingival sides of the appliances, or along any other combination of two sides. Moreover, the height of the guides may be reduced to avoid interference with the guides or appliances associated with adjacent teeth, and optionally the distance of the lingual wall of the channel 44 from the adjacent surface of the model tooth 34 could be less than the distance of the lingual wall of the archwire slot 48 from the model tooth 34. In these instances, the construction of the appliance holder as described below is revised as necessary to facilitate use of the holder with such guides.

Preferably, the guides 40 as shown in FIGS. 3-5 are spaced apart from each other a distance in a mesial-distal direction that is only slightly larger than the overall, mesial-distal width of a base 50 of the appliance 46. However, to facilitate insertion of the appliance 46 in the space between the guides 40, the guides 40 preferably extend at an angle away from each other as the outer ends of the guides are approached as can be appreciated, for example, by reference to FIG. 4. In FIG. 4, the combined angle between the inner, facing walls of the two guides 40 is approximately 10 degrees, although other angles are also possible.

Each of the guides 40 is preferably connected by detachable structure to the associated model tooth 34. In the embodiment shown in FIGS. 3-5, each of the guides 40 include four cylindrical legs 52 that integrally connect the body 42 to the associated model tooth 34. The legs 52 can be readily fractured by urging the associated body 42 in a direction away from the appliance 46 using a pivotal, swinging motion in order to detach and separate the guide 40 from the model tooth 34 when desired.

Figure 6:
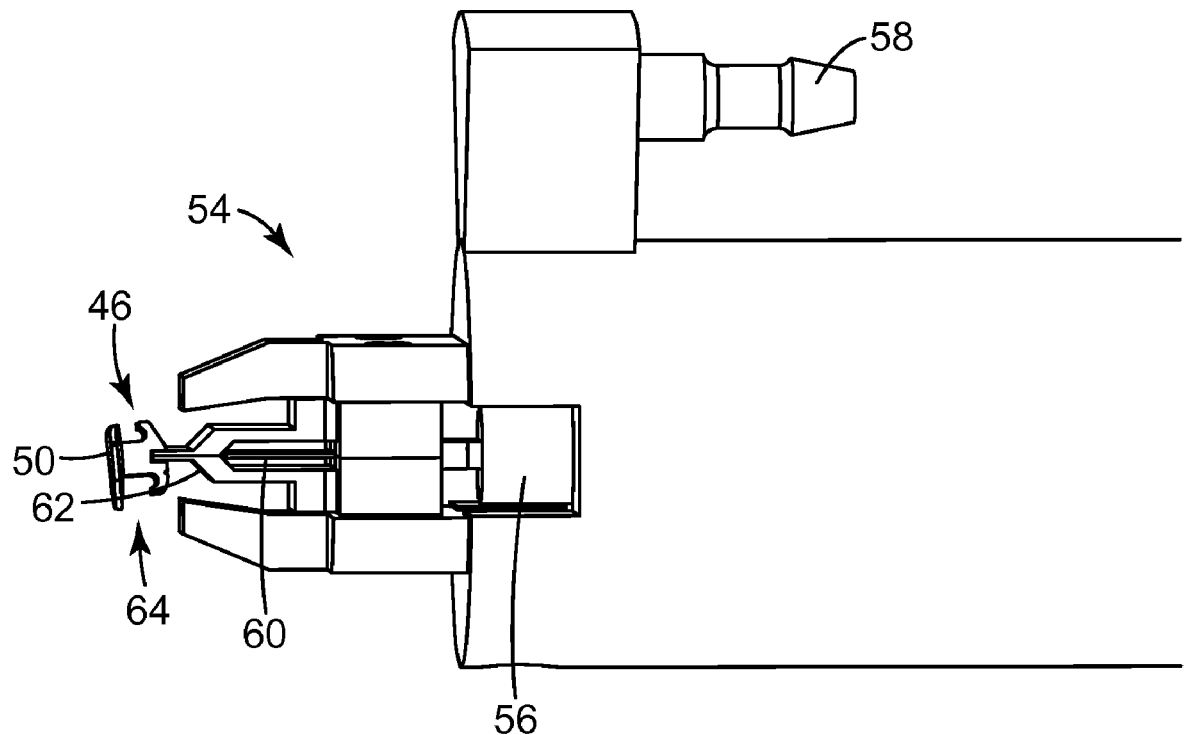
FIG. 6 is a fragmentary perspective view of one type of holder that may be used for placing appliances on the model, wherein the holder includes a gauge that is received in an archwire slot of the appliance.
Figure 7:
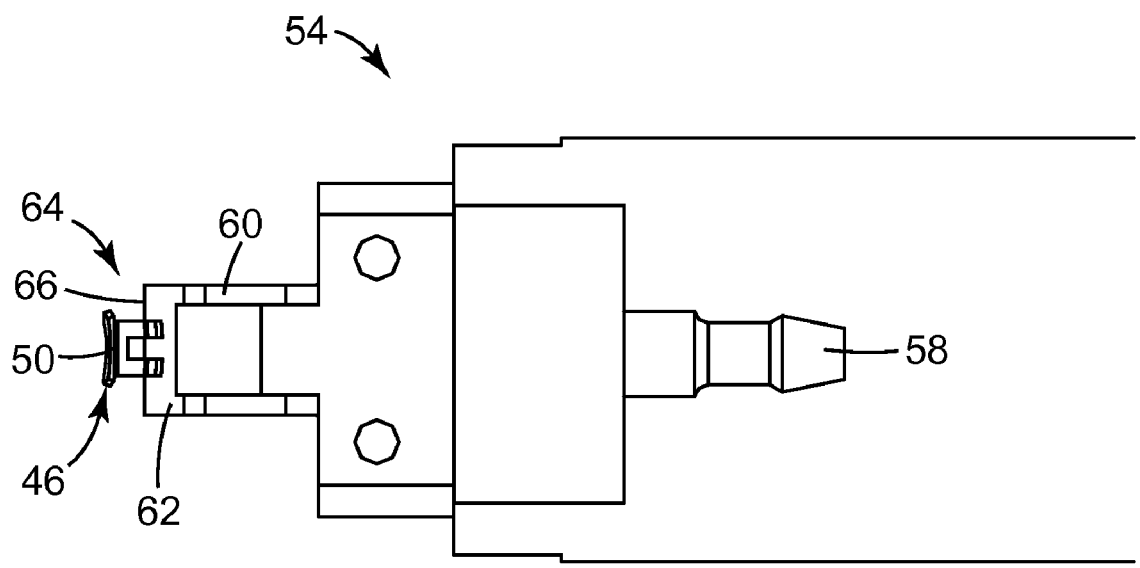
FIG. 7 is a fragmentary view somewhat similar to FIG. 6 except looking in a direction toward the top of the holder and an occlusal side of the appliance.
Figure 8:
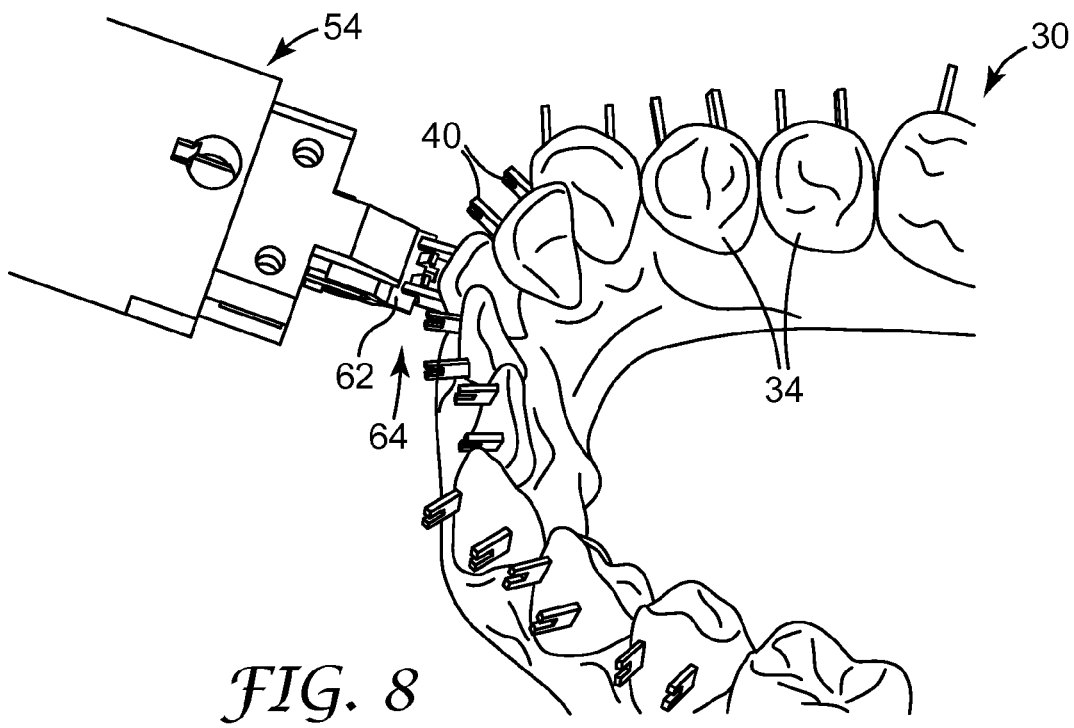
FIG. 8 is a fragmentary perspective view showing an exemplary use of the holder illustrated in FIGS. 6 and 7 in placing the appliance on the dental arch model shown in FIG. 2.

FIGS. 6-8 illustrate an exemplary holder 54 that may be used to position and place the appliances 46 onto the dental arch model 30. The holder 54 includes an air-operated piston and cylinder assembly 56 (FIG. 6) that receives air for actuation of the piston through inlet 58. The piston of the assembly 56 is connected to a blade expander 60 that is positioned between two resilient gripper blades 62. The two blades 62 together represent a placement gauge 64, and serve to releasably hold an appliance 46 as well as to guide the appliance 46 to a proper position by use of a releasable, mating fit with the guides 40.

The gripper blades 62 of the holder 54 have outer portions that converge toward each other and then continue in parallel planes to outer ends 66 (see, e.g., FIG. 7). As air is directed to the piston and cylinder assembly 56, the piston extends and moves the blade expander 60 toward the converging portions of the blades 62 to move, in turn, the outer ends 66 in directions away from each other. As the outer ends 66 move away from each other, they come into secure contact with occlusal and gingival walls of the archwire slot 48 and thereby serve to securely hold the appliance 46 during appliance placement.

Other constructions for the holder 54 are also possible. For example, the holder 54 may include a piezo-electric element, such as a rectangular prismatic bar, that expands in an occlusal-gingival direction when sufficient voltage is applied to the element. As the element expands, it contacts the occlusal and gingival walls of the archwire slot 48 to securely grip the appliance 46. In this manner, the appliance 46 can be gripped or released on demand by operation of an electric switch that could be placed on a handle of the holder or in a remote location such as a foot pedal.

Once the appliance 46 is gripped by the outer ends 66 of the holder 54, the appliance 46 is placed between guides 40 of the alignment structure in order to temporarily bond the appliance 46 to the associated model tooth 34 as described in block 114. However, before placement of the appliances 46 on the dental arch model 30, a release agent is applied to the model teeth 34 and gingival tissue 32 as described in block 112. An example of a suitable release agent is water soluble polyvinyl alcohol, such as "PA0810" from PTM&W Company of Santa Fe Springs, Calif.

A bonding composition (not shown) is placed between the base 50 of the appliance 46 and the model tooth 34. Preferably, the bonding composition is a light-curable composition such as a light curable adhesive, and the adhesive is coated across the base 50 of each appliance 46. Optionally, the appliances 46 are adhesive precoated appliances that have a layer of light-curable adhesive applied by the manufacturer to the base 50 of each appliance 46, such as APC Plus brand appliances and APC II brand appliances from 3M Unitek Corporation. Examples of adhesive coated appliances are described in U.S. Pat. Nos. 5,015,180, 5,172,809, 5,354,199, 5,429,229, 6,183,249 and 6,960,079. The appliances 46 may be made of any suitable material such as metal (e.g., stainless steel), ceramic (e.g., translucent polycrystalline alumina or monocrystalline alumina) or plastic (e.g., translucent polycarbonate) or combinations thereof.

If the appliances 46 are not coated with adhesive in advance by the appliance manufacturer, the bonding composition is applied to the base 50 of each appliance 46 immediately before placement of the appliance 46 on the arch model 30. Suitable bonding compositions include orthodontic adhesives such as composites, compomers, glass ionomers and resin-modified glass ionomers. Examples of light-curable adhesives include Transbond XT brand and Transbond LR brand adhesives from 3M Unitek Corporation. Examples of chemical curing adhesives include Concise brand adhesive and Multi-Cure brand glass ionomer cement from 3M Unitek Corporation.

As the appliance 46 is moved toward the guides 40, the outer ends 66 of the holder 54 move into the channel 44 of each body 42. The holder 54 continues to move toward the arch model 30 until such time as the outer ends 66 have seated against the lingual wall of the channels 44. Preferably, the distance between the occlusal and gingival walls of the channel 44 of each body 42 is only slightly larger than the distance between the occlusal and gingival walls of the archwire slot 48 so that the outer ends 66 are matingly received in the channel 44 without undue possible lateral movement or "slop". An example of a suitable tolerance or difference between such distances is plus or minus 0.1 mm.

When the appliance 46 is properly oriented relative to the guides 40, the three walls of the archwire slot 48 have an orientation in 3D space that is coplanar with the respective three walls of the channel 44 of each guide 40, such that the guides 40 have known physical characteristics relative to the appliance 46. Since the outer ends 66 of the holder 54 when fully expanded against the occlusal and gingival walls of the archwire slot 48 have a known physical characteristic relative to the appliance 46 (in this embodiment, known orientations in 3D space relative to the archwire slot 48) as well as a known physical characteristic relative to the guides 40 (in this embodiment, known orientations in 3D space relative to the channels 44), the holder 54 accurately places the appliances 46 relative to the guides 40 with high precision. In addition, since the software used to design the virtual guides 40 is able to orient the virtual guides in precise, desired positions relative to the associated virtual tooth, the model guides 40 as produced by rapid prototyping are accurately oriented relative to the desired position of the associated appliances 46 on the model teeth 34. Additionally, since the orientation of the guides 40 is determined by the orientation of the associated appliance 46, the software can change the orientation of the guides 40 if the desired position of the appliance 46 is changed.

Moreover, the guides 40 can be designed by the software to support the appliance 46 in one or more angular orientations that may deviate from a typical orientation of the appliance relative to the associated tooth. As an example, the guides 40 can be designed to provide supplemental tip and/or torque (i.e., tip and/or torque that differs from the amount of tip and/or torque that is provided by the appliance 46) by orienting the channels 44 in appropriate directions. Optionally, the guides can be designed to orient the base 50 of the appliance 46 in an angular orientation such that the base 50 is not uniformly spaced by an adhesive layer from the adjacent tooth surface of the model tooth 34. For example, the guides 40 could be constructed to enable the adhesive layer to be thicker along the mesial side of the base 50 as compared to the distal side of the base 50 so that the associated tooth of the patient will tend to be rotated about its long axis during the course of treatment.

Preferably, the software automates the design of the guides 40 by reference to geometric parameters particular to the selected appliances 46. For example, a database containing information for each appliance such as its mesial-distal width, in-out dimension, torque and angulation can be established, and the software can design the guides 40 based on design templates and information in the database.

Other constructions for the holder 54 are also possible. For example, opposite sides of the outer end 66 of the holder 54 may be stepped and/or oriented at an angle in correspondence with a stepped shape and/or orientation of the guides 40 as mentioned earlier. In addition, opposite sides of the outer ends 66 may include features that engage structure of the guides 40 and/or the appliance 46 to provide proper orientation of the appliance 46 in a mesial-distal direction. In instances where the latter option is used, the guides 40 may be spaced further apart from each other and need not contact the base 50 of the appliance 46 for mesial-distal positioning. As one example, the outer ends 66 may include a protrusion that is adapted for snug, mating reception in the occlusal-gingival or "vertical" channel that is located between mesial and distal tiewings of a twin tiewing bracket.

Once the outer ends 66 of the holder 54 are firmly seated in the channels 44 of the guides 40, the piston of the piston and cylinder assembly 56 is retracted to shift the blade expander 60 in a direction away from the outer tip portions of the gripper blades 62. As the blade expander retracts, the resilient gripper blades 62 (preferably made of tool steel) self-move toward each other such that the outer ends 66 no longer tightly engage the occlusal and gingival walls of the archwire slot 48. The holder 54 can then be moved in a direction away from the appliance 46 to detach the outer ends 66 from the archwire slot 48.

Next, the bonding composition is allowed to harden and form a custom bonding pad for the base 50 as described in block 116. The resulting bonding pad is advantageous in that it has a contour that precisely matches the contour of the model tooth 34 and hence matches the contour of the respective tooth of the patient. This matching shape facilitates the subsequent bond of the appliance to the tooth and reduces the likelihood that the appliance 46 will become unintentionally detached from the tooth during the course of treatment.

Figure 9:
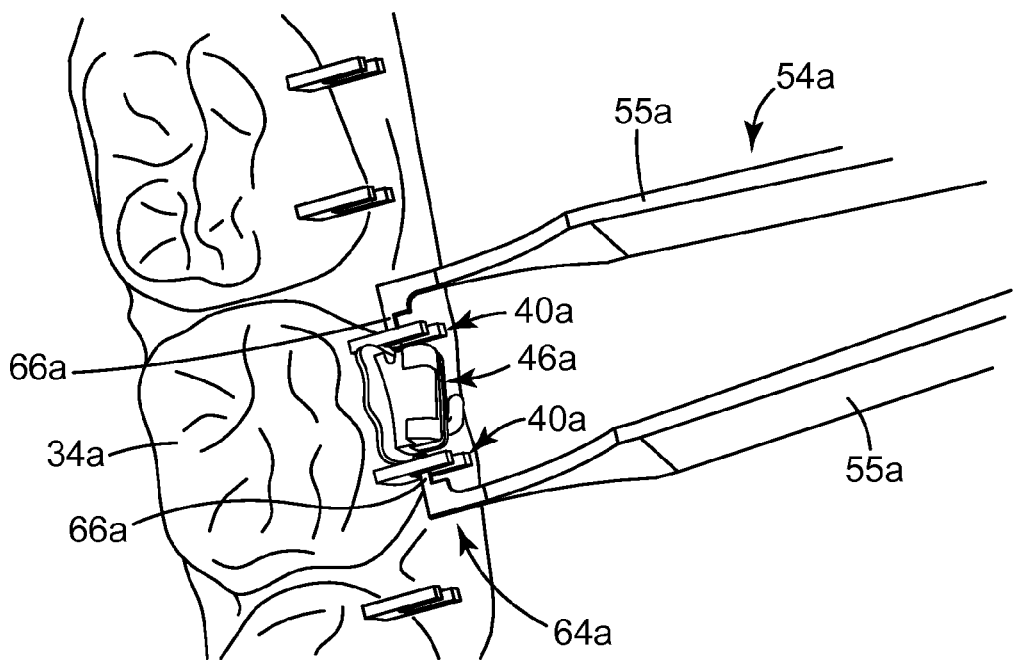
FIG. 9 is a fragmentary perspective view of an alternative holder for placing orthodontic appliances on the dental arch model, wherein the holder is particularly useful for placing appliances that have a closed archwire slot such as buccal tubes.

An orthodontic appliance holder 54a according to another embodiment of the invention is illustrated in FIG. 9 and is particularly useful in connection with the placement of orthodontic appliances that have an archwire slot that is closed along its labial side. Examples of such appliances include buccal tubes, which have an archwire slot that resembles an elongated passage. This passage has open mesial and distal ends and often has a rectangular shape in cross-sectional view. An exemplary buccal tube appliance 46a is also shown in FIG. 9.

The holder 54a includes a pair of arms 55a, each of which includes an outer, generally "L"-shaped end portion that terminates at an outer end 66a. The opposed outer ends 66a extend toward each other and have a rectangular cross-sectional shape that is constructed for mating reception into a rectangular passage of buccal tube appliance 46a. The outer ends 66a collectively represent a gauge 64a for aligning and placing the buccal tube appliance 46a in its proper position on the corresponding model tooth 34a.

The arms 55a are movable by finger pressure in directions toward each other, and sufficiently resilient to self-move away from each other when finger pressure is relieved. When in a relaxed orientation, the arms 55a are sufficiently spaced from each other such that the distance between the facing tips of the outer ends 66a is greater than the overall distance between the mesial and distal openings of the archwire slot of the buccal tube appliance 46a. When it is desired to place the buccal tube appliance 46a on the model tooth 34a, the user guides the outer ends 66a to respective positions adjacent the mesial and distal openings of the archwire slot of the buccal tube appliance 46a, and then applies pressure to the arms 55a to urge the arms 55a together. As the outer ends 66a move toward each other, the outer ends 66a slide into the archwire slot of the buccal tube appliance 46a so that the latter can be manipulated as needed. The matching rectangular cross-sectional shapes of the outer ends 66a and the archwire slot of the appliance 46a ensures that the appliance 46a does not rotate about the longitudinal axis of the archwire slot during such movement and placement.

As shown in FIG. 9, a pair of spaced apart guides 40a is integrally connected to the replica molar tooth 34a. The guides 40a are similar to the guides 40 in that the guides 40a each have a channel with occlusal, lingual and gingival walls. These occlusal, lingual and gingival walls are designed and constructed to be oriented in co-planar relation with the occlusal, lingual and gingival walls respectively of the archwire slot of the buccal tube appliance 46a when the buccal tube appliance 46a is in its desired orientation on the model tooth 34a.

During placement of the appliance 46a, the outer ends 66a of the holder 54a are received in the channels of the guides 40a. The appliance 46a is moved in a lingual direction toward the replica tooth 34a until the outer ends 66a contact the bottom or lingual wall of the channels of the guides 40a. Once this contact is established, pressure on the arms 55a is released and the arms 55a spread open. As the arms 55a move away from each other, the outer ends 66a move out of the archwire slot of the appliance 46a, and thus enable the holder 54a to be moved away from the replica tooth 34a without disturbing the position of the appliance 46a.

The use of the appliance holders 54, 54a in combination with guides 40, 40a has been described above as a manual procedure that is easily carried out by hand. Alternatively, however, the appliance holders 54, 54a may be adapted for use with automated robotic machinery for grasping the appliances 46, 46a and placing the same on the arch model 30. Software programmed for the robotic machinery can provide instructions to retrieve each appliance 46, 46a from a designated storage location for appliances 46, 46a in inventory such as a rack system that holds the appliances 46, 46a in a known orientation. Once the robotic machinery has moved the holder 54, 54a coupled to the machinery to retrieve an appliance 46, 46a from inventory, the robotic machinery maneuvers the holder 54, 54a to move the appliance 46, 46a into a position so that the outer ends 66, 66a of the holder 54, 54a contact the guides 40, 40a.

Although robotic machinery in theory can be operated with great precision to place appliances 46, 46a on replica teeth 34, 34a, the use of alignment structure such as guides 40, 40a is an advantage in that small errors in the position of the holder 54, 54a can be tolerated. So long as the robotic machinery provides the holder 54, 54a with sufficient freedom to move small, limited distances during placement of the appliances 46, 46a, the guides 40, 40a can serve to properly position the holder 54, 54a as the appliance 46, 46a is placed on the model teeth 34, 34a.

Figure 10:
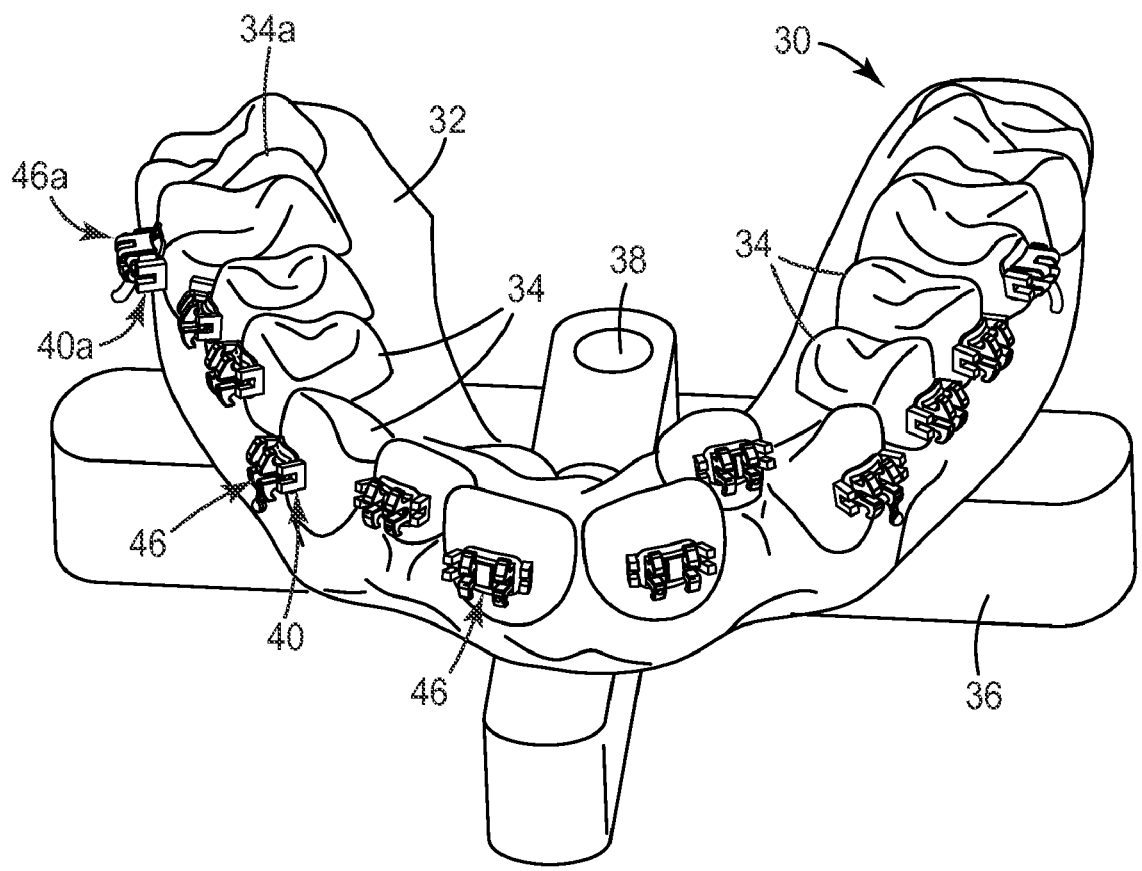
FIG. 10 is a perspective view of the dental arch model shown in FIG. 2 along with a set of orthodontic appliances that have been placed on the dental arch model using the guides.

FIG. 10 is a view somewhat similar to FIG. 2, except in FIG. 10 all of the appliances 46, 46a have been placed between pairs of respective guides 40, 40a on the arch model 30. Optionally, the bonding composition used for creating the bonding pads and for temporarily bonding each appliance 46, 46a to the arch model 30 is cured or partially cured before the next appliance 46, 46a is placed on the arch model 30. As yet another option, all of the appliances 46, 46a are placed on the arch model 30 before curing or partially curing any of the bonding composition.

If the appliances 46, 46a are made of metal or another opaque material and if a light-curable adhesive is used as a bonding composition, it is preferable to expose the dental arch model 30 to a curing light for a relatively long amount of time in order to ensure that the bonding composition has sufficiently hardened. A hand-held curing unit may be used, such as Ortholux XT brand curing unit from 3M Unitek Corporation, by directing the light for approximately 10 seconds toward the mesial side and 10 seconds toward the distal side of each appliance. A LED hand-held curing unit may also be used, such as Ortholux LED brand curing unit from 3M Unitek Corporation, by directing the light for approximately 5 seconds toward the mesial side and 5 seconds toward the distal side of each appliance. As an alternative, a light curing chamber may be used, such as Triad 2000 visible light curing system from Dentsply, by activating the light in the curing chamber for at least 10 minutes. Preferably, the material used to make the arch model 30 transmits actinic radiation to facilitate light in reaching all portions of the bonding composition beneath the base 50 of the appliances 46, 46a.

Preferably, before activating the light source, any adhesive flash that has extruded from the sides of the appliance base 50 is removed using a scaler, probe, swab, brush or high-velocity air stream. Alternatively, however, the adhesive flash may be removed after the adhesive has been partially hardened. Additionally, as another option, the holders 54, 54a may include a support for supporting an air nozzle to supply the high-velocity air stream for removing flash as mentioned above.

The guides 40, 40a are also removed at this time by moving the guides 40, 40a in either a mesial or distal direction away from the adjacent appliance 46, 46a until the legs 52 of the guides 40, 40a fracture and detach from remaining portions of the model 30. Preferably, the legs 52 fracture at a location directly adjacent the adjoining surfaces of the model tooth 34, 34a so that no portion of the legs 52 that remain will protrude from the model tooth surfaces.

As yet another option, the compressible materials described in pending U.S. patent application Ser. No. 11/551, 823 filed Oct. 23, 2006 and entitled "Dental Articles, Methods and Kits Including a Compressible Material" (Cinader, Jr.) may be used instead of the bonding compositions for creating the bonding pads mentioned above. Advantageously, when using this option the need for removal of adhesive flash is eliminated. In this option, the guides 40, 40a are spaced closer together and the appliances 46, 46a are held in place by friction-fit between the guides 40, 40a while the tray is formed as described in the paragraphs that follow in those instances when the bonding composition is not hardened prior to making the tray. Alternatively, when the bonding composition is hardened prior to making the tray, the friction fit can be eliminated. To minimize the depth of the impression of the guides 40, 40a in the tray matrix material, the guides 40, 40a are relatively short in length, or are shortened (e.g. by fracture or otherwise) after the appliances 46, 46a are in place.

Figure 11:
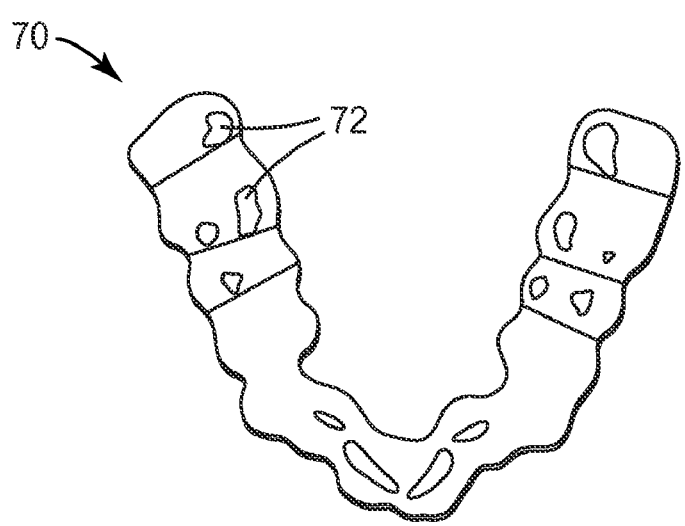
FIG. 11 is a bottom view of an occlusal stop member that is used for making the indirect bonding tray.

FIG. 11 is a bottom view of an occlusal stop member 70 that is preferably made in a rapid prototyping manufacturing process (as described in block 110) simultaneously with the rapid prototyping manufacture of the dental arch model 30 and the tray molding vessel (described below). The occlusal stop member 70 has a flat top surface and a bottom surface with shapes such as recesses 72 that match the shapes of the occlusal tips of the patient's dental arch. In the embodiment shown in FIG. 11, the occlusal stop member 70 has a recess or recesses corresponding to only some of the teeth in the dental arch, although it is also possible to construct an occlusal stop member that has one or more recesses corresponding to each tooth of the dental arch.

Other variations are also possible. For example, the occlusal stop member may extend only along a portion of the dental arch instead of along the entire dental arch as illustrated in FIG. 11. As another option, a plurality of stop members may be provided. For example, a stop member could be provided for each of the two molar regions and a third stop member could be provided for the anterior region of the dental arch. When more than one stop member is provided, the stop members can be spaced apart from each other and optionally connected together.

Figure 12:
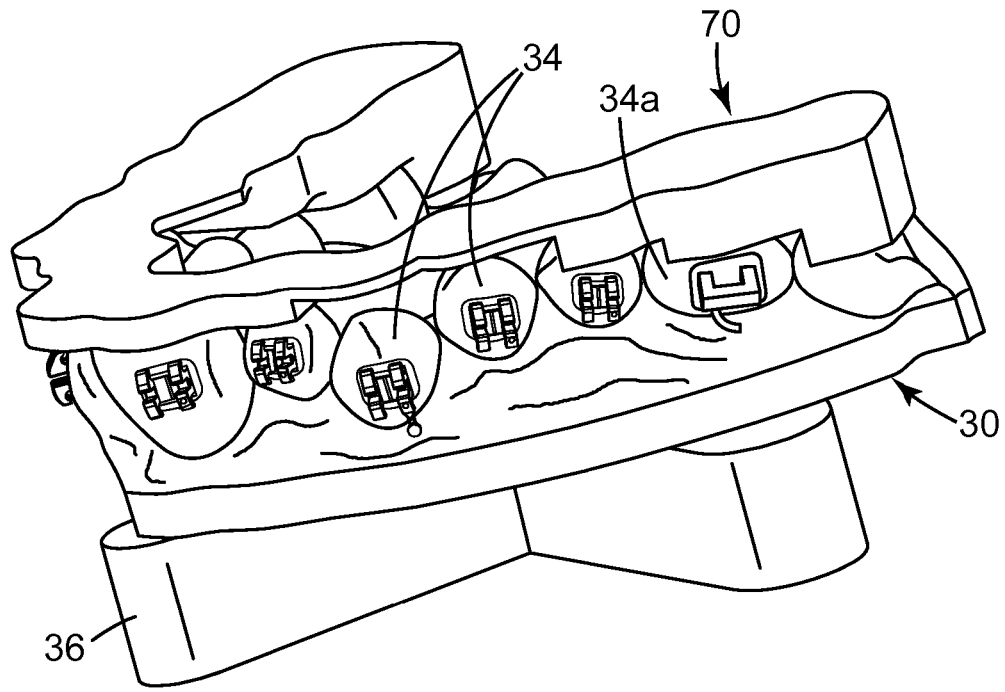
FIG. 12 is a perspective view of the dental arch model and appliances shown in FIG. 10 but looking in a different direction, wherein the guides of the arch model have been removed and the occlusal stop member depicted in FIG. 11 has been placed over occlusal surfaces of the model teeth.

FIG. 12 is an illustration of the arch model 30 after such time as the guides 40, 40a have been detached from the corresponding replica teeth 34, 34a and the adhesive flash has been removed. In FIG. 12, the occlusal stop member 70 has also been placed over the occlusal surfaces of the teeth 34, 34a. Because the recesses 72 match the shape of the corresponding cusp tips of the replica teeth 34, 34a, the occlusal stop member 70 can be firmly seated on the arch model 30 in such a manner that little, if any, relative lateral movement is possible between the occlusal stop member 70 and the arch model 30 in an occlusal reference plane.

Subsequently, and as described in block 120, a first matrix material is applied to the orthodontic appliances 46, 46a. In the embodiment shown in FIG. 13, the first matrix material 74 has been applied to all of the appliances 46, 46a in the manner of a continuous strip with larger dabs of adhesive over each appliance 46, 46a and smaller necked sections joining the larger dabs, as might occur when a dispenser for the first matrix material 74 is moved from one appliance 46, 46a to the next. However, as another option, the first matrix material 74 may be applied to each appliance 46, 46a as a separate, discreet dab. As still another option, the first matrix material 74 may be applied in the manner of a continuous strip having a relatively uniform width along the entire length of the arch model 30 while covering each of the appliances 46, 46a. Preferably, the first matrix material 74 contacts the occlusal, facial, gingival, mesial and distal sides of the appliances 46, 46a. Optionally, but not necessarily, a portion of the first matrix material 74 also contacts sections of the facial sides of the replica teeth 34, 34a that extend along the base 50 of the appliances 46, 46a.

Preferably, the first matrix material 74 has a relatively low viscosity before hardening so that intimate contact between the first matrix material 74 and each appliance 46, 46a is assured. In this manner, the first matrix material 74 is able to substantially penetrate in the various recesses, cavities and other structural features of each appliance 46, 46a so that a secure connection between the appliances 46, 46a and the matrix material 74 can be established.

An example of a suitable first matrix material 74 is Emiluma brand silicone material from Shofu Dental Corporation. The matrix material 74 has a viscosity before curing that is preferably less than about 80,000 cp, more preferably less than about 25,000 cp and most preferably less than about 8,000 cp. Once hardened, the matrix material 74 has a tensile stress at 20 percent elongation (according to ASTM D 412) that is in the range of about 31,000 to about 496,000 Pascal, more preferably in the range of about 62,000 to about 248,000 Pascal and most preferably in the range of about 112,000 to about 136,000 Pascal, and has a tensile stress at 50 percent elongation that is in the range of about 91,000 to about 1,460,000 Pascal, more preferably in the range of about 183,000 to about 730,000 Pascal and most preferably in the range of about 329,000 to about 402,000 Pascal. An example of a suitable first matrix material 74 has a tensile stress at 20 percent elongation of about 124,000 Pascal and a tensile stress at 50 elongation of about 365,000 Pascal.

Figure 14:
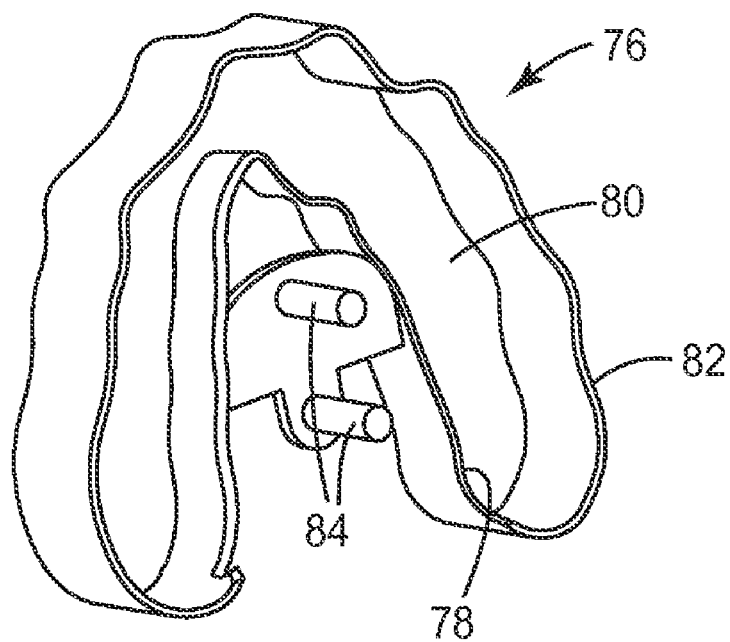
FIG. 14 is a perspective view looking toward the top of a tray molding vessel that is adapted to receive a quantity of a second matrix material.

FIG. 14 is a perspective view of a tray molding vessel or casting vessel 76 having an internal cavity 78. Preferably, the tray molding vessel 76 is made by rapid prototyping as described in block 110 simultaneously with rapid prototyping of the dental arch model 30 and the occlusal stop member 70. Optionally, the bottom of the cavity 78 is flat and has a shape that matches the flat top surface of the occlusal stop member 70. In this embodiment, side walls 82 of the vessel 76 that define the cavity 78 extend in a perpendicular direction away from the flat bottom 80, and terminate at the opening of the cavity 78 in a reference plane that lies parallel to the bottom 80. Preferably, the shape of the cavity 78 is minimized as much as practical in order to reduce the overall size of the resulting indirect bonding tray as well as to reduce the amount of material needed to make the tray and the vessel 76.

As an additional option, indicia such as tracking numbers and/or patient data may be formed by rapid prototyping in the tray molding vessel 76, the occlusal stop member 70 and/or the dental arch model 30 during the rapid prototyping process of forming the latter components. Moreover, such indicia can be formed in mirror-image along the inner surfaces of the bottom 80 and/or the side walls 82, so that an imprint presenting a positive image of the indicia is later formed when the indirect bonding tray is made as described below. Alternatively, however, a set of pre-manufactured molding vessels may be used in place of the custom molding vessel described above. For example, a set of vessels could be made to match various standardized archforms, such as the ovoid, standard and square archforms known in the art as described by Drs. McLaughlin, Bennett and Trevisi. In addition, each of the vessels associated with standard archforms could be pre-manufactured in certain sizes, such as small, medium and large.

Figure 15:
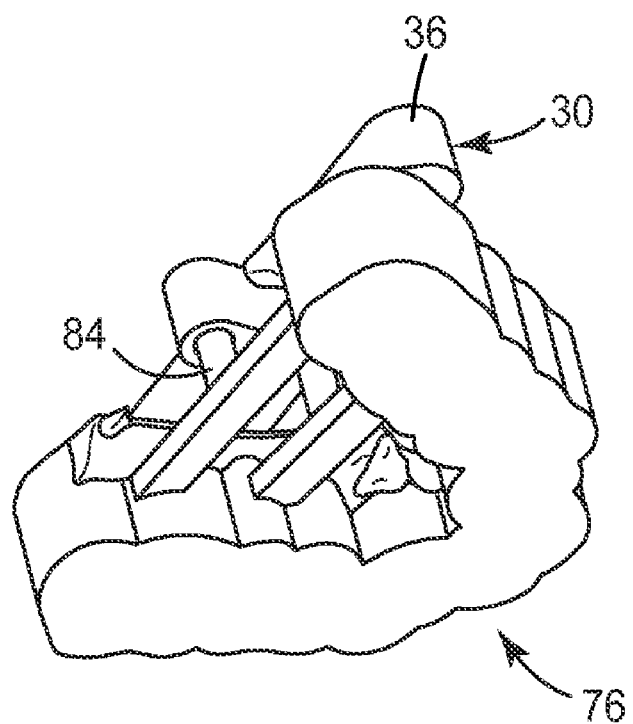
FIG. 15 is a view of the dental arch model shown in FIG. 13 along with the occlusal stop member after the model has been inverted and placed into the vessel of FIG. 14 containing the second matrix material.
Figure 16:
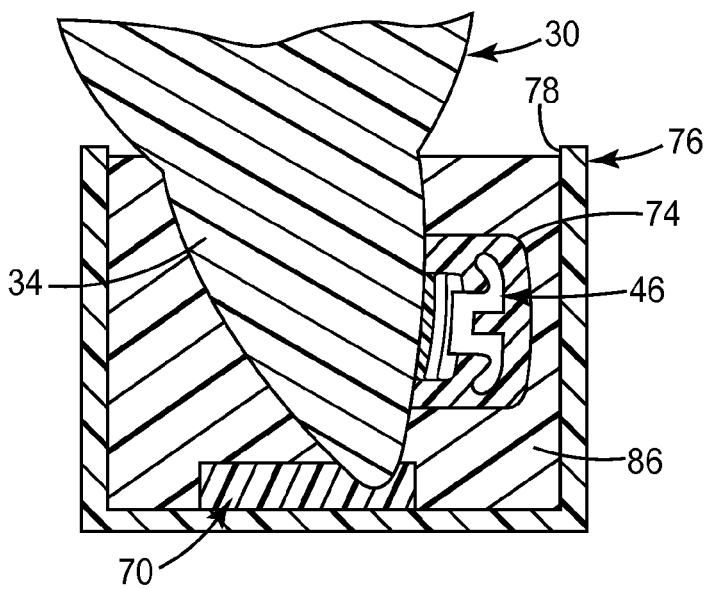
FIG. 16 is a cross-sectional view taken in a reference plane lying perpendicular to the curved longitudinal axis of the dental arch model, showing one of the appliances bonded to one of the model teeth and additionally showing the first matrix material, second matrix material and occlusal stop member that together comprise the indirect bonding tray.

The tray molding vessel 76 also has a framework that includes alignment structure that, in the illustrated embodiment, comprises a pair of spaced apart posts 84. The posts 84 are matingly received in the alignment holes 38 of the arch model substrate 36 when the arch model 30 is placed into the cavity 78 of the tray molding vessel 76. In this manner, the orientation of the arch model 30 and the resulting indirect bonding tray is fixed relative to the orientation of the cavity 78 in a desired, predetermined spatial relationship. Other constructions for the alignment structure of the tray molding vessel 76 and the arch model substrate 36 are also possible, such as a single post and a single matching hole having non-circular cross-sectional shapes, or other combinations of posts and holes, or a reversal of such components. A quantity of a second matrix material 86 (not shown in FIGS. 14 and 15; see FIGS. 16 and 17) is dispensed into in the cavity 78. The arch model 30, together with the appliances 46, 46a and the occlusal stop member 70, is then inverted and placed into the cavity 78 as described in block 122. FIG. 16 is a cross-sectional view of an exemplary model tooth 34, appliance 46, the first matrix material 74 and the occlusal stop member 70 when received in the cavity 78 of the tray molding vessel 76 containing the second matrix material 86.

As depicted in FIG. 16, the second matrix material 86 contacts the labial, occlusal and lingual surfaces of the replica teeth 34 except in areas covered by the first matrix material 74 and the occlusal stop member 70. In addition, the second matrix material 86 extends over and preferably completely surrounds the first matrix material 74 except in underlying areas of the arch model 30. Optionally, the second matrix material 86 extends over the distal ends of the first matrix material 74 adjacent the model molar teeth. The second matrix material 86 also preferably surrounds the occlusal stop member 70 except for those regions of the occlusal stop member 70 that are in contact with the arch model 30. In this embodiment, the stop member 70 is spaced from the first matrix material 74 and separated from the first matrix material 74 by the second matrix material 86.

An example of a suitable second matrix material 86 is Memosil 2 brand vinyl polysiloxane material from Heraeus Kulzer, Inc. The second matrix material 86 has a viscosity before curing that is preferably less than about 1,000,000 cp, more preferably less than about 100,000 cp and most preferably less than about 8,000 cp. Once hardened, the second matrix material 86 has a tensile stress at 20 percent elongation (according to ASTM D 412) that is in the range of about $0.4 \times 10^6$ to about $6.5 \times 10^6$ Pascal, more preferably in the range of about $0.8 \times 10^6$ to about $3.3 \times 10^6$ Pascal and most preferably in the range of about $1.1 \times 10^6$ to about $1.4 \times 10^6$ Pascal, and has a tensile stress at 50 percent elongation that is in the range of about $0.8 \times 10^6$ to about $12.5 \times 10^6$ Pascal, more preferably in the range of about $1.6 \times 10^6$ to about $6.2 \times 10^6$ Pascal and most preferably in the range of about $2.8 \times 10^6$ to about $3.4 \times 10^6$ Pascal. An example of a suitable second matrix material 86 has a tensile stress at 20 percent elongation of about $1.3 \times 10^6$ Pascal and a tensile stress at 50 elongation of about $3.1 \times 10^6$ Pascal.

The second matrix material 86 preferably has a composition that is different than the composition of the first matrix material 74 and after hardening exhibits a tensile stress at 20 percent elongation that is preferably greater than the tensile stress at 20 percent elongation that is exhibited by the first matrix material 74 after hardening. The second matrix material 86 after hardening exhibits a tensile stress at 20 percent elongation that exceeds the tensile stress at 20 percent elongation of the first matrix material 74 after hardening preferably by a ratio in the range of about 2:1 to about 40:1, more preferably by a ratio in the range of about 5:1 to about 20:1 and most preferably by a ratio in the range of about 7:1 to about 12:1. Preferably, the second matrix material 86 chemically bonds to the first matrix material 74 with a relatively high bond strength.

The occlusal stop member 70 is relatively inflexible and has a Shore A hardness that is greater than the Shore A hardness of either of the first matrix material 74 or the second matrix material 86. Preferably, the occlusal stop member 70 has a Shore A hardness that is greater than about 72, more preferably has a Shore A hardness that is greater than about 90, even more preferably has a Shore D hardness that is greater than about 60 and most preferably has a Shore D hardness that is greater than about 75. An example of a suitable hardness is 72 Shore A hardness.

Optionally, the occlusal stop member 70 chemically bonds to the second matrix material 86 as the latter is cured. In addition, or in the alternative a thin layer of the second matrix material 86 extends over the flat top of the occlusal stop member 70 opposite the side of the stop member 70 facing the arch model 30 in order to physically capture and connect the stop member 70 to the second matrix material 86 once hardened. Moreover, the occlusal stop member 70 may include outwardly-extending barbs or other structure that provides undercut areas for mechanically interlocking the occlusal stop member 70 to the second matrix material 86 once the latter has hardened.

As an alternative, the occlusal stop member 70 is inserted into the cavity 78 of the molding vessel 76 and placed in contact with the vessel bottom 80 before the arch model 30 and the appliances 46, 46a are placed in the vessel 76. In this alternative, a quantity of the second matrix material is dispensed into the cavity 78 either before or after the arch model 30 and the appliances 46, 46a are placed in the cavity 78. As one example, the stop member 70 has a peripheral shape that matches the shape of the side walls 82 so that the stop member 70 is properly aligned with the arch model 30 when the latter is received in the cavity 78. As another example, the stop member 70 has a peripheral shape that is somewhat smaller than the shape of the side walls 82 and instead engages alignment structure of the vessel 76 extending in the cavity 78 for proper, subsequent alignment of the stop member 70 with arch model 30.

An indirect bonding tray 88, comprising the appliances 46, 46a, the occlusal stop member 70 and the matrix materials 74, 86, is thus formed once the second matrix material 86 has hardened. The tray 88 is then removed from the molding vessel 76 as indicated by block 124 and the bonding tray 88 is then removed from the arch model 30. The use of the release agent as mentioned above helps facilitate detaching the tray 88 from the molding vessel 76 and detaching the tray 88 (including the appliances 46, 46a) from the arch model 30. Excess material of the tray 88 is then trimmed as desired as described in block 126 and the tray 88 is inspected before use.

Figure 17:
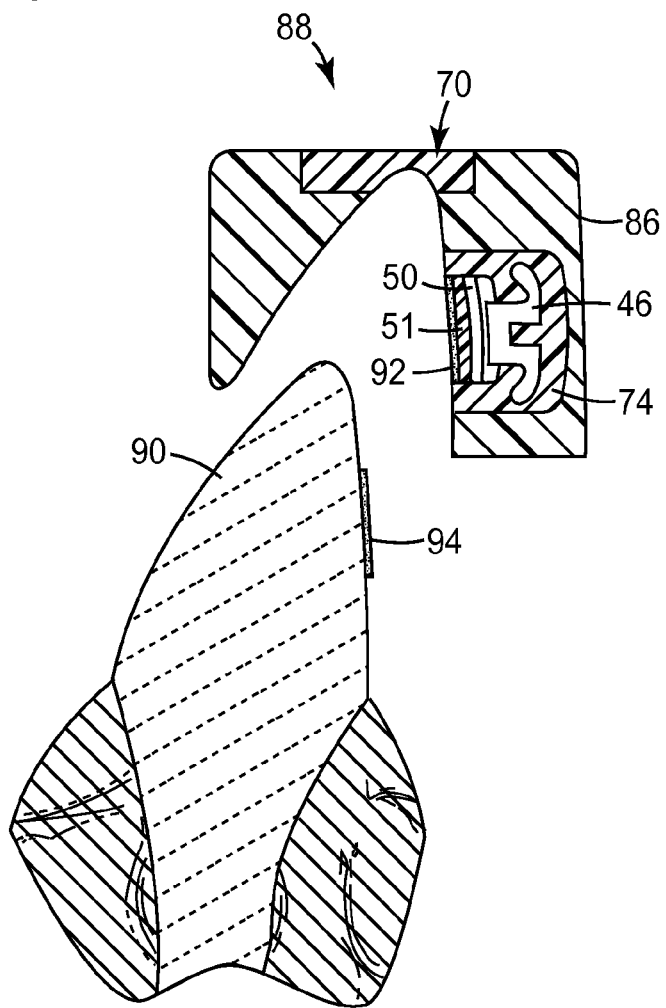
FIG. 17 is a side cross-sectional view of the indirect bonding tray illustrated in FIG. 16 after the tray has been detached from the dental arch model and trimmed, and further depicting the tray as it might appear immediately before placing the tray over the patient's dental arch.

As shown in FIG. 17, the hardened second matrix material 86 presents a lingual, occlusal and facial outer surface that represents the lingual, occlusal and facial sides respectively of the tray 88. Preferably, the outermost gingival edge of the tray 88 along the facial side of the tray 88 is located only slightly below the gingival sides of the appliances and spaced in an occlusal direction from the patient's gingival margin when the tray 88 is received in place on the patient's dental arch. Preferably, the outermost gingival edge of the tray 88 along the lingual side of the tray 88 is spaced about 0.5 mm from the patient's gingival margin when the tray 88 is received in place on the patient's dental arch. Such construction facilitates urging the appliances 46, 46a against the patient's teeth during a bonding procedure. The outermost gingival edges of the tray 88 along its facial and lingual sides may be substantially straight or scalloped to follow the contours of the gingival margin.

A description of an exemplary use of the indirect bonding tray 88 will now be provided with reference to FIG. 17. First, the patient's teeth that are to receive the appliances 46, 46a are isolated using cheek retractors, tongue guards, cotton rolls, dry angles and/or other articles as needed. An exemplary tooth 90 is depicted in FIG. 17. The teeth 90 are then thoroughly dried using pressurized air from an air syringe. Etching solution (such as Transbond XT brand etching gel from 3M Unitek Corporation) is then dabbed onto the teeth 90 in the general area that is to be covered by the appliances 46, 46a, taking care to prevent the etching solution from flowing into interproximal contacts or engaging the skin or gingiva.

After the etching solution has remained on the selected tooth surfaces for a period of approximately 30 seconds, the solution is rinsed away from the teeth 90 with a stream of water for 15 seconds. The patient's teeth are then dried by the application of pressurized air from an air syringe (for example, for a time period of 30 seconds) and excess water is removed by suction. Alternatively, the teeth may be simultaneously etched and primed with Transbond Plus Self Etching Primer from 3M Unitek Corporation. Care should also be undertaken to ensure that the saliva does not come into contact with the etched enamel surfaces. Cotton rolls or other absorbent devices are replaced as needed, again making sure that the saliva does not contact the etched enamel. Air from the air syringe may then be applied to the teeth 90 again to ensure that the teeth 90 are thoroughly dried.

Next, a bonding adhesive is applied to the bonding pad of the appliances 46, 46a and/or the selected areas of the patient's teeth 90. Optionally, the bonding adhesive is a two-component adhesive as depicted in FIG. 17. For example, a first component 92 is Transbond brand XT Primer or Transbond brand MIP Moisture Insensitive Primer, and a second component 94 is Transbond brand Plus Self Etching Primer, both from 3M Unitek Corporation. The first component 92 is applied to the bonding pad (designated 51 in FIG. 17) connected to the base 50 of the appliances 46, 46a and the second component 94 is applied to the area of the patient's tooth 90 that is to receive the corresponding appliance 46, 46a.

After the first component 92 has been applied to the bonding pad and the second component 94 has been applied to corresponding areas of the patient's teeth 90, the tray 88 is then positioned over the corresponding teeth 90 and seated, optionally with a swinging, hinge-type motion. Since the shape of the cavity presented by the matrix materials 74, 86 and the occlusal stop member 70 together match the shape of the underlying teeth, the appliances 46, 46a are simultaneously seated against the underlying teeth 90 at precisely the same locations corresponding to the previous respective positions of the appliances 46, 46a on the arch model 30.

When the tray 88 is constructed using the preferred materials mentioned above, it has been observed that the tray 88 seems to "snap" in place as the tooth cavities in the tray 88 are received over teeth of the patient's dental arch. Since the interior cavities of the tray 88 defined by surfaces of the matrix materials 74, 86 and the occlusal stop member 70 have shapes that are complemental to the shapes of the patient's teeth 90, the tray 88 may be sufficiently stiff to press the appliances 46, 46a against the teeth 90 as the adhesive cures without the application of external pressure. However, as an option, external pressure may be applied to the occlusal and facial surfaces of the tray 88 until such time as the bonding adhesive has sufficiently hardened. For example, finger pressure may be used to firmly press the appliances 46, 46a against the facial surfaces of the patient's teeth 90.

Other examples of suitable two-component chemical curing adhesives include Sondhi brand Rapid-Set indirect bonding adhesive, Unite brand adhesive and Concise brand adhesive, all from 3M Unitek Corporation. As an alternative, a resin-modified glass ionomer cement may be employed. As yet another option, a photocurable adhesive may be used, such as Transbond XT brand adhesive, Transbond LR brand adhesive and Transbond Moisture Insensitive Primer, all from 3M Unitek Corporation. Other examples of suitable photocurable adhesive materials are described in U.S. Pat. No. 7,137,812 (Cleary et al.) as well as in pending U.S. Patent Publication Nos. 2005/0175965 (Craig et al.), 2005/0175966 (Falsafi et al.) and 2005/0176844 (Aasen et al.). The indirect bonding tray 88 may also be packaged with appliances that are precoated with adhesive by the manufacturer, as described in U.S. Pat. No. 7,137,812 (Cleary et al.). An alternative method for applying primer to the patient's teeth 90 is described in U.S. Pat. No. 7,168,950 (Cinader, Jr., et al.)

Once the bonding adhesive has hardened, the bonding tray 88 is carefully removed from the patient's dental arch. Optionally, a hand instrument such as a scaler may be used to help hold each appliance 46, 46a against the surface of the respective tooth 90 of the patient as the matrix material 74 is peeled away from the appliances 46, 46a. However, in instances where the first matrix material 74 is relatively soft or otherwise readily releases from the appliances 46, 46a, the use of a scaler to help avoid fracturing the fresh adhesive bond is optional. As yet another option, the tray 88 may include a "rip cord" as described in U.S. Pat. No. 7,020,963 (Cleary et al.) in order to fracture the tray 88 before removal from the oral cavity.

After the indirect bonding tray has been released from the patient's dental arch, an archwire is placed in the archwire slots of the appliances 46, 46a and ligated in place. Suitable ligation devices include tiny, elastic O-rings as well as sections of wire that are tied in a loop around the appliances 46, 46a. As another option, the appliances 46, 46a may be self-ligating appliances that include a latch for releasably engaging the archwire such as those described in U.S. Pat. No. 6,302,688 (Jordan et al.) and PCT Publication No. WO02/089693.

Figure 18:
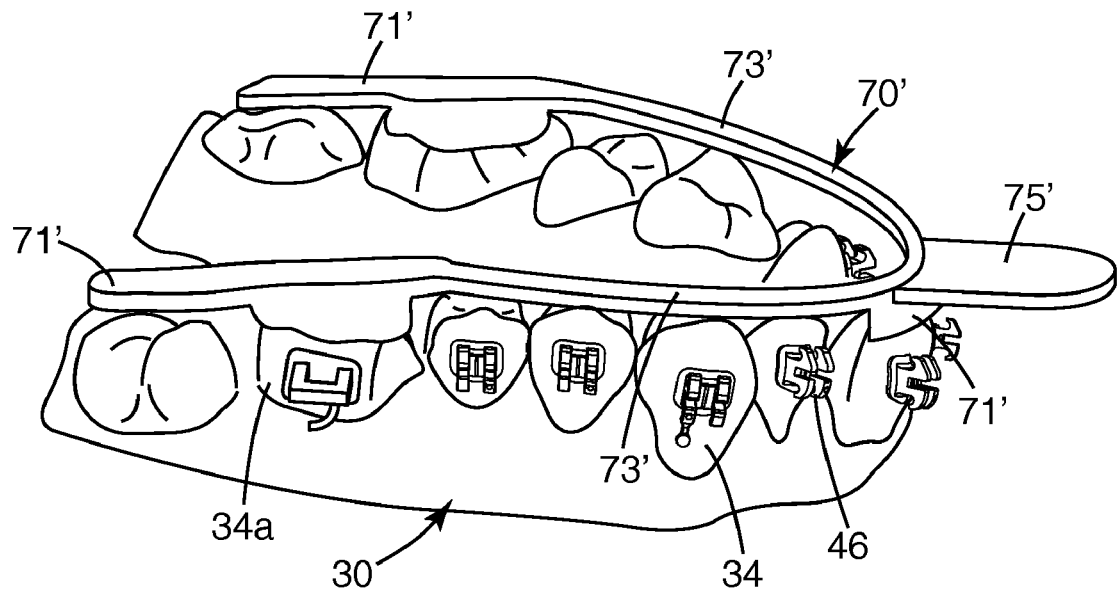
FIG. 18 is a perspective view of an occlusal stop member according to another embodiment of the present invention, wherein the occlusal stop member has been placed over a dental arch model that has received a set of orthodontic appliances.

An occlusal stop member 70' according to another embodiment of the invention is illustrated in FIG. 18. In this embodiment, the occlusal stop member 70' is a single, unitary component but includes four distinct, spaced-apart sections 71' in contact with the occlusal tips of model teeth 34, 34a. Two of the sections 71' are located over posterior regions of the arch model 30 for contact with replica molar teeth 34a, while two sections 71' are in contact with two model lower incisor teeth 34. Although not shown in the drawings, each of the sections 71' includes recesses (similar to recesses 72) that matingly receive occlusal tips of the underlying model teeth 34, 34a.

The occlusal stop member 70' also includes an elongated, flexible connecting section 73' that interconnects the anterior sections 71' and the posterior sections 71'. The connecting section 73' has a smaller cross-sectional area and consequently is more flexible than the anterior sections 71' and the posterior sections 71'. In this embodiment, the connecting section 73' does not contact the model teeth 34, 34a and does not include surfaces that match model tooth surfaces.

In addition, the occlusal stop member 70' includes a handle 75' that extends in a facial direction away from the anterior sections 71'. The handle 75' extends past both of the matrix materials once the indirect bonding tray is made, and provides a convenient point of leverage for use by the practitioner when placing the indirect bonding tray onto the patient's dental arch and for removing the indirect bonding tray from the patient's oral cavity after the appliances have been bonded in place. In this embodiment, the tray molding vessel (such as vessel 76) has an opening near the middle of the outer side wall 82 to receive the handle 75' when the occlusal stop member 70' is placed in the vessel. Additionally, the tray molding vessel preferably has a rounded bottom (instead of a flat bottom such as bottom 80) that receives the occlusal stop member 70' in relatively close relation so that the overall size of the resulting bonding tray is reduced.

The flexible connecting section 73' facilitates bending of the resulting indirect bonding tray during use. In particular, the connecting section 73' reduces the amount of finger pressure that might otherwise be necessary for the practitioner to squeeze the posterior regions of the resulting indirect bonding tray in directions toward each other in order to facilitate passage of the indirect bonding tray through the patient's mouth and into the oral cavity. Once the bonding tray is inside the oral cavity, pressure on posterior regions of the tray is released and the connecting section 73' enables the posterior regions of the resilient bonding tray to spring apart and move back to their original configuration so that the tray can then be placed in contact with the patient's teeth.

Preferably, the posterior sections 71' only contact the tooth that is adjacent the distal-most tooth in each side of the dental arch. Preferably, the anterior sections 71' only contact the two mesial-most teeth of the dental arch. Preferably, all of the sections 71' are spaced a distance of at least 0.5 mm from the adjacent appliance 46, but have a thickness that is not greater than necessary so that the resulting thickness of the bonding tray is not unduly affected.

Figure 19:
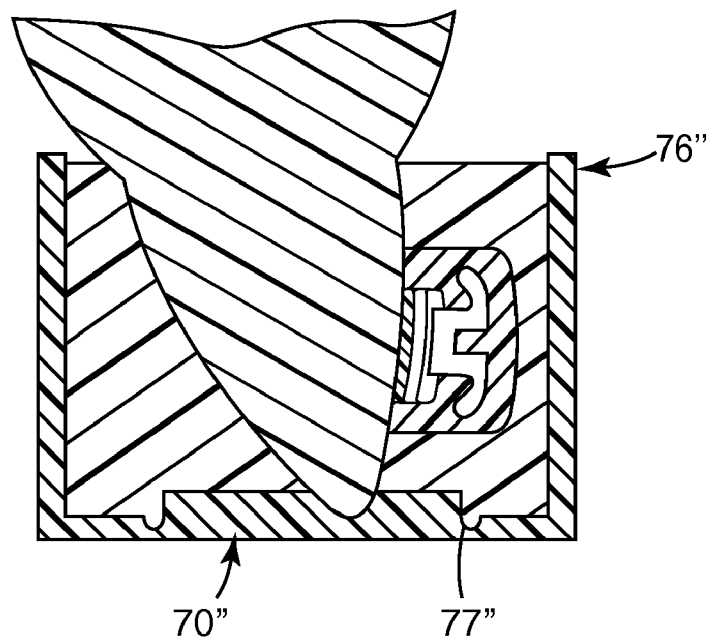
FIG. 19 is a cross-sectional view showing a molding vessel and occlusal stop member constructed in accordance with another embodiment of the invention.

FIG. 19 is a cross-sectional view of an occlusal stop member 70" and a tray molding vessel 76" that are constructed in accordance with another embodiment of the invention. In this embodiment, the occlusal stop member 70" is initially integral with the tray molding vessel 76" and the occlusal stop member 70" and the tray molding vessel 76" are formed together during rapid prototyping. A line of weakness 77" surrounds the occlusal stop member 70" and defines the boundary between the occlusal stop member 70" and the tray molding vessel 76". After the matrix materials are formed and hardened in a manner similar to the description provided above in connection with FIG. 16 and the tray is removed from the model dental arch, the molding vessel 76" is fractured along the line of weakness 77" and discarded.

As another option, any of the occlusal stop members 70, 70', 70" described above may include a spaced-apart series of arms that each extend in a gingival direction toward a respective appliance 46, 46a. For example, the arms may include an outer end section that is received in the occlusal-gingival or "vertical" channel between tiewings of the appliances 46. These outer end sections help stiffen the resulting tray in rotational directions about its curved central axis and consequently help press the appliances 46 against the patient's tooth surfaces during a bonding procedure.

In all of the embodiments described above, the use of the guides in combination with the holders is an advantage in that placement of the orthodontic appliances is carried out by physical registration of the archwire slot to a structural feature of the dental arch model or its substrate. The modeling software described above can provide instructions for rapid prototype manufacturing of the arch model including the guides so that accurate placement of the appliances can be provided without the use of templates, measuring instruments or the like. Moreover, since the principles of straight-wire treatment are based on the orientation of the archwire slot, registration of the archwire slot to the dental arch models as described herein helps to ensure that the teeth are aligned in their desired positions at the conclusion of treatment.

In addition to the various embodiments described above, other features, constructions and methods are possible. For example, structure could be added to the bonding tray for controlling moisture control during the bonding procedure, such as described in pending U.S. patent application entitled "APPARATUS AND METHODS FOR CONTROLLING MOISTURE DURING ORTHODONTIC INDIRECT BONDING PROCEDURES" (U.S. Ser. No. 11/422,613) and pending U.S. patent application entitled "ORTHODONTIC INDIRECT BONDING TRAY WITH MOISTURE CONTROL" (U.S. Ser. No. 11/422,614). Receptacles could be provided in the bonding tray to receive a source of light, such as described in pending U.S. patent application entitled "METHODS AND APPARATUS FOR BONDING ORTHODONTIC APPLIANCES USING PHOTOCURABLE ADHESIVE MATERIAL", filed on even date herewith. Radio-frequency identification (RFID) tags could be used to track patient-specific materials throughout the manufacturing of the bonding trays, as described in U.S. Published Patent Application No. 2006/0134580 entitled "RFID TRACKING OF PATIENT-SPECIFIC ORTHODONTIC MATERIALS". Markers may be used to register virtual and physical dental arches, such as described in U.S. Published Patent Application No. 2007/0031774 entitled "REGISTERING PHYSICAL AND VIRTUAL TOOTH STRUCTURES WITH MARKERS".

Example

Figure 13:
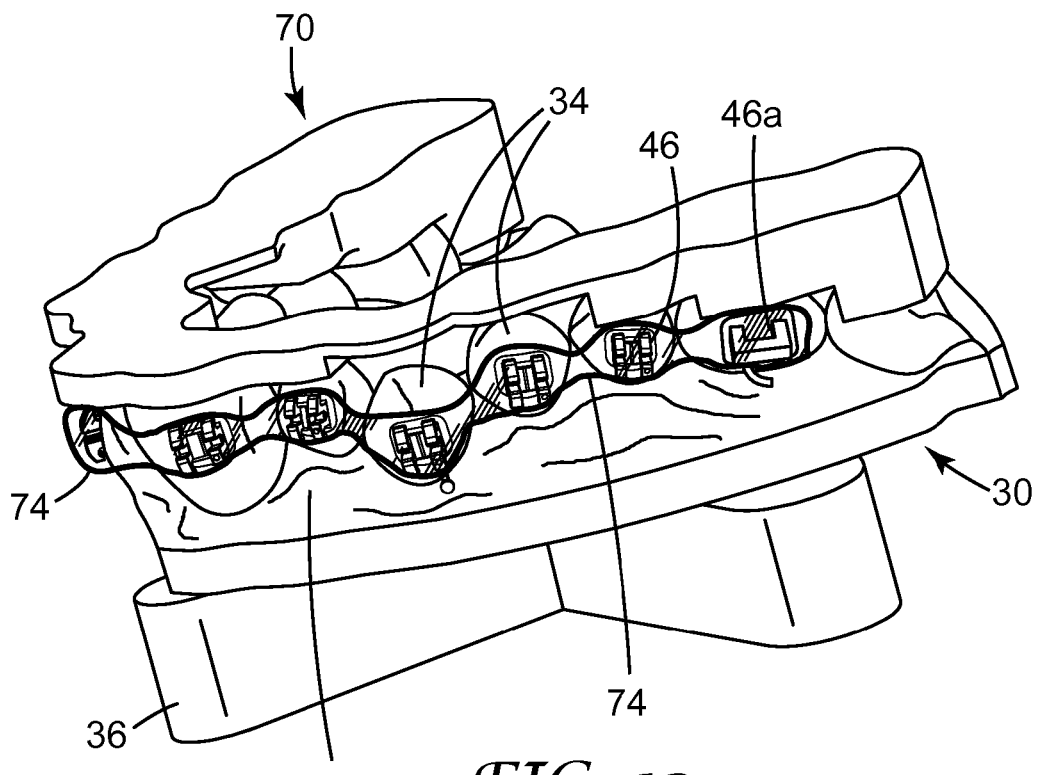
FIG. 13 is a view somewhat similar to FIG. 12 except that a first matrix material has been applied to the orthodontic appliances.

Experiments were conducted to compare the transfer accuracy (i.e., the accuracy of appliance placement) of the bonding trays of the present invention with bonding trays of other constructions. Three digital data files, representing the shape of three different dental arches, were obtained. Each of the three data files was used to make a bonding tray and molding vessel according to the methods described above in connection with bonding tray 88 and molding vessel 76, but using an occlusal stop member similar to the occlusal stop member 70' illustrated in FIG. 18. To make these three trays, the first matrix material was the Emiluma brand silicone material and the second matrix material was the Memosil 2 brand vinyl polysiloxane material as mentioned above, and sufficient first matrix material was applied to the bracket appliances to generally appear as shown in FIG. 13. The occlusal stop member and tray molding vessel were made using the FullCure 720 printing material.

For purposes of comparison, five other indirect bonding trays were also constructed for each of the three dental arches. Comparative bonding trays A were constructed according to the methods described in U.S. Publication No. 2006/0223031, using the RTV silicone material, the bite registration material and the 1.5 mm polycarbonate sheet described in Table I below. Bonding trays B were constructed by placing discreet dabs of the silicone material described in Table I over each of the appliances, and then applying the vinyl polysiloxane material over the silicone material and the model teeth using a hand-held dispenser.

Comparative bonding trays C were constructed by first applying a layer of the vinyl polysiloxane material as described in Table I over the bracket appliances and the model teeth, then placing the sheet material as described in Table I over the polysiloxane material. The assembly was then placed in a pressure forming device (Biostar brand thermoformer, from Great Lakes Orthodontics) to form the tray. Comparative bonding trays D were constructed by placing the sheet material described in Table I over the appliances and the model teeth, and pressure forming the sheet material using the thermoformer mentioned above. After cooling the sheet material, a second sheet of sheet material (see also Table I) was placed over the first sheet material and assembly was then placed in the thermoformer to form the tray. Comparative bonding trays E were constructed in a manner similar to comparative trays C, except that the thickness of the sheet material for making bonding trays E was greater.

TABLE I

Comparative Tray Construction

| Tray | Material | Source |
|---|---|---|
| A | Silicone RTV 615 | General Electric |
|  | 3M ESPE Express brand Bite Registration Material (Fully Cured), part no. 6060J | 3M Espe |
|  | 1.5 mm Polycarbonate outer shell (Makrolon brand, part no. 8574K5) | Sheffield Plastics |
| B | Emiluma beads on brackets | Shofu |
|  | Memosil II over Emiluma and teeth | Kulzer Dental |
| C | Affinity brand Crystal Clear Matrix Impression Material over brackets | Clinicians' Choice |
|  | Clear Splint BioCryl brand sheet material, 0.5 mm thick, for outer tray | Great Lakes Orthodontics |
| D | BioPlast brand sheet material, 1.5 mm thick, for inner tray | Great Lakes Orthodontics |
|  | Clear Splint BioCryl brand sheet material, 0.75 mm thick, for outer tray | Great Lakes Orthodontics |
| E | Affinity brand Crystal Clear Matrix Impression Material over brackets | Clinicians' Choice |
|  | Clear Splint BioCryl brand sheet material brand sheet material, 0.75 mm thick, for outer tray | Great Lakes Orthodontics |

To determine placement accuracy of the comparative trays as well as the trays constructed according to the present invention, the digital data files were used to make a first model arch for each tray with guides 40 as described above, as well as a second model arch of identical construction for each tray except lacking the guides. The software described above was used to determine desired position coordinates for virtual bracket appliances on the model teeth as well as to design the construction of the guides. Orthodontic bracket appliances were then placed on each of the first model arches using a hand-held appliance holder in conjunction with the guides. After the appliances were bonded to the model teeth, the guides were removed. The position coordinates of each appliance in a global coordinate system as bonded to the first model arch were determined and recorded.

The trays were then made over the appliances and first models and detached with the appliances from the models. To simulate bonding to a patient's teeth, each of the trays was then placed on one of the second model arches and the appliances were bonded to the model teeth of the second model arches. The bonding trays were then detached from the appliances and the second model arches. Next, the position coordinates of each appliance in a global coordinate system as bonded to the second model dental arch were determined. As also described in more detail below, average tray transfer errors were then obtained by comparing the position coordinates of the appliances as bonded to the first model arch to the position coordinates of the appliances as bonded to the second dental model arch.

Measurement of Actual Appliance Coordinates

A measurement appendage 99 (see FIG. 20) for each appliance was prepared by machining a flat, rectangular section of aluminum to a thickness matching the occlusal-gingival dimension of the archwire slot and a width matching the overall, mesial-distal dimension of the archwire slot of each bracket appliance 46. One side of each appendage 99 was laser etched to present four circles arranged in a rectangular array as well as a circular target in the middle of each circle. The surface of the appendage 99 was anodized to make it non-reflective and reduce the possibility of errors due to reflective light. The appendage 99 was then placed in the archwire slot, moved to a position to flatly engage the lingual wall of the archwire slot and checked to confirm a snug, mating fit. The mesial and distal sides of the appendage 99 were aligned with the mesial and distal ends respectively of the bracket appliance 46.

A SmartScope ZIP 250 brand measurement apparatus (from Optical Gaging Products, Inc.) was then used to determine the coordinates of each of the four circular targets relative to the origin of the pedestal or substrate (such as substrate 36). The positioning coordinates of the brackets as bonded to the model teeth was then compared to the desired position coordinates of the bracket appliances as virtually determined by the software, using the following coordinate systems:

Appliance Archwire Slot Coordinate System

Appliance positions were represented by placing a local Cartesian coordinate system at the middle and bottom (i.e., in the mesial-distal center of the archwire slot and the occlusal-gingival center of the archwire slot, and in a position on the lingual wall of the archwire slot, using the following designations:

1. X—Toward distal direction for upper patient left brackets and lower patient right bracket and vice versa. This will align with the archwire slot for non-angulated brackets but will be at the angle of angulation with the angulated brackets.
2. Y—Toward gingival direction following the long axis of the tooth.
3. Z—Toward facial direction. This will always be perpendicular to the lingual plane of the archwire slot (or bottom wall of the archwire slot).

Appliance Base Coordinate System

A transformation matrix was used to relate the appliance slot coordinate system to the appliance base coordinate system. The appliance base coordinate was at the center of the appliance base (which was also on the model tooth surface).

Global Pedestal Coordinate System and Tooth Model

The appliance base coordinate was related to the global pedestal coordinate by another transformation matrix. The origin of the global pedestal coordinate system was located at the center of the base of the pedestal. The arch model was mounted on top of the pedestal, and the following designations were employed:

+y points toward gingival direction of the arch.
+z points toward the anterior of the arch.
+x points horizontally: toward patient's left if maxillary, toward patient's right if mandibular.

Transformation Matrices and Coordinate Transformations

Two transformation matrices, pedestal to appliance base and appliance base to archwire slot, were used to transform a pedestal coordinates $(x_p, y_p, z_p)$ to the appliance archwire slot coordinates $(x_s, y_s, z_s)$ as $$\begin{bmatrix} x_s \\ y_s \\ z_s \\ 1 \end{bmatrix} =$$

-continued $$\begin{bmatrix} a'_{11} & a'_{12} & a'_{13} & x'_o \\ a'_{21} & a'_{22} & a'_{23} & y'_o \\ a'_{31} & a'_{32} & a'_{33} & z'_o \\ 0 & 0 & 0 & 1 \end{bmatrix}_{base \to slot} \begin{bmatrix} a_{11} & a_{12} & a_{13} & x_o \\ a_{21} & a_{22} & a_{23} & y_o \\ a_{31} & a_{32} & a_{33} & z_o \\ 0 & 0 & 0 & 1 \end{bmatrix}_{pedestal \to slot} \begin{bmatrix} x_p \\ y_p \\ z_p \\ 1 \end{bmatrix}$$

Where $a'_{ij}$'s, $a_{ij}$'s were the component of angular transformation and $(x'_o, y'_o, z'_o)$ and $(x_o, y_o, z_o)$ were the origin of the base and slot coordinate system respectively.

Writing the equation in a short form as $$S = T_{base \to slot} T_{pedestal \to base} P = T_{pedestal \to slot} P$$

Or inversely $$P = T_{pedestal \to slot}^{-1} S$$

Appliance Origin Calculation for Virtual Model

Appliance origin of the virtual model relative to the pedestal coordinate system was obtained by substituting $$\begin{bmatrix} 0 \\ 0 \\ 0 \\ 1 \end{bmatrix} \text{ for } \begin{bmatrix} x_p \\ y_p \\ z_p \\ 1 \end{bmatrix}$$

in the above equation as $$\begin{bmatrix} x_v \\ y_v \\ z_v \\ 1 \end{bmatrix} = \begin{bmatrix} a'_{11} & a'_{12} & a'_{13} & x'_o \\ a'_{21} & a'_{22} & a'_{23} & y'_o \\ a'_{31} & a'_{32} & a'_{33} & z'_o \\ 0 & 0 & 0 & 1 \end{bmatrix}_{base \to slot} \begin{bmatrix} a_{11} & a_{12} & a_{13} & x_o \\ a_{21} & a_{22} & a_{23} & y_o \\ a_{31} & a_{32} & a_{33} & z_o \\ 0 & 0 & 0 & 1 \end{bmatrix}_{pedestal \to slot} \begin{bmatrix} 0 \\ 0 \\ 0 \\ 1 \end{bmatrix}$$

Appliance Origin Calculation for Physical Model

Figure 20:
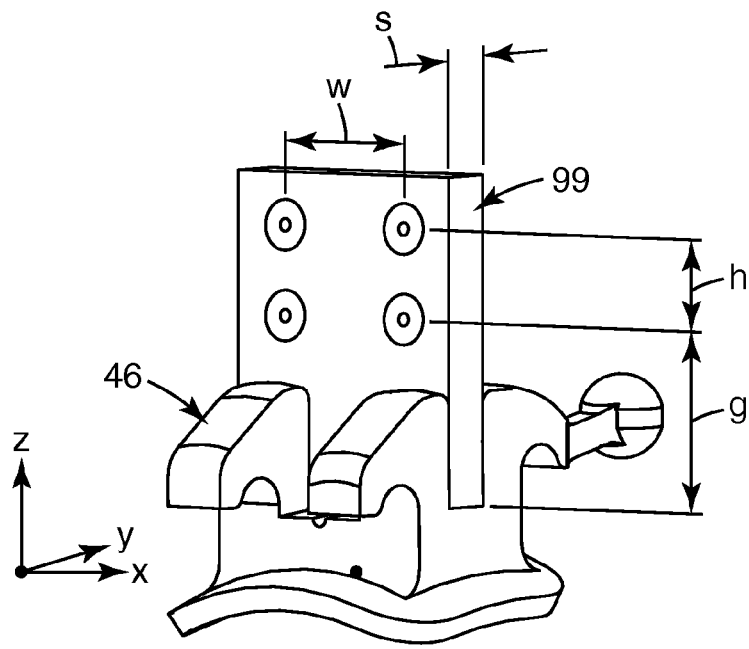
FIG. 20 is an illustration showing an exemplary orthodontic appliance along with an appendage used to determine positioning errors.

The SmartScope apparatus mentioned above was used to measure the coordinates of four circular targets (designated Points 1 through 4) relative to the pedestal origin. FIG. 20 illustrates an appendage 99 adapted for snug, mating fit in the archwire slot of bracket appliance 46. Points 1 through 4 were located on the surface of the appendage and arranged in a rectangular array. FIG. 20 also depicts the dimensions w, h, g and s along with the coordinate system for the origin of appliance 46.

Before finding the origin of the appliance archwire slot coordinate, the unit vector en was calculated, at mid-point on the line connecting Points 1 and 4 and perpendicular to the appendage, from the coordinates measured by the Smart-Scope apparatus:

$$e_n = \frac{u_{46} \times u_{56}}{|u_{46} \times u_{56}|} \text{ where}$$

$u_{ij} = u_i - u_j$ and $$u_5 = \frac{u_2 + u_3}{2}$$

$$u_6 = \frac{u_1 + u_4}{2}$$

The origin of the appliance archwire slot coordinate system in the middle of archwire slot relative to the pedestal coordinate system was then $$u_0 \begin{bmatrix} x_a \\ y_a \\ z_a \end{bmatrix} = u_6 - u_{56} \frac{g}{h} - \frac{se_n}{2}$$

Where g was the distance in the z direction from the appliance origin to Points 1 and 4, h was the distance in the z direction between Points 1 and 2 and s was the archwire slot size measured in the y direction.

Comparison of Appliance Locations between Virtual and Actual

The differences of coordinates (3 translational) between the measured bonded appliance locations and the virtual, intended appliance locations was then tabulated and graphed among different bracket appliances and the actual and virtual models.

Translational Differences

The translational differences in the bracket position for each bracket between the virtual (v) and actual (a) using the pedestal coordinate system can be expressed as:

$$\begin{bmatrix} \Delta x_{a-v} \\ \Delta y_{a-v} \\ \Delta z_{a-v} \end{bmatrix} = \begin{bmatrix} x_a \\ y_a \\ z_a \end{bmatrix} - \begin{bmatrix} x_v \\ y_v \\ z_v \end{bmatrix}$$

where $$\begin{bmatrix} x_a \\ y_a \\ z_a \end{bmatrix} \text{ and } \begin{bmatrix} x_v \\ y_v \\ z_v \end{bmatrix}$$

are the coordinates of the origin of the bracket in the pedestal coordinate system in the actual and virtual models respectively.

The translational differences in the bracket position for each bracket between the virtual (v) and actual (a) using the bracket slot coordinate system can be expressed as:

$$\begin{bmatrix} mesial - distal \\ occlusal - gingival \\ labial - lingual \end{bmatrix} =$$

-continued $$\begin{bmatrix} \Delta MD_{a-v} \\ \Delta OG_{a-v} \\ \Delta LL_{a-v} \end{bmatrix}_{slot} = \begin{bmatrix} \Delta x_{a-v} \\ \Delta y_{a-v} \\ \Delta z_{a-v} \end{bmatrix}_{slot} = T^{-1}_{pedestal \to slot} \begin{bmatrix} \Delta x_{a-v} \\ \Delta y_{a-v} \\ \Delta z_{a-v} \end{bmatrix}_{pedestal}$$

The above equation was used to calculate the translational difference between the first actual bracket position of the initial bonding and the virtual bracket position. It was also used to calculate the translational difference between the second actual bracket position after tray transfer and the same virtual bracket position.

The magnitude of the translational difference for each bracket between the first position and the second position was calculated from $$\Delta_i = \left( \sqrt{(\Delta MD_{a-v,1} - \Delta MD_{a-v,2})^2 + (\Delta OG_{a-v,1} - \Delta OG_{a-v}, 2)^2 + (\Delta LL_{a-v,1} - \Delta LL_{a-v,2})^2} \right)_i$$

where $\Delta_i$ is the magnitude of the translational difference for bracket i.

The averaged translational difference of the brackets on the whole arch is then $$\overline{\Delta} = \frac{1}{N} \sum_{i=1}^{N} \Delta_i$$

where N is the total number of brackets in the arch.

Figure 21:
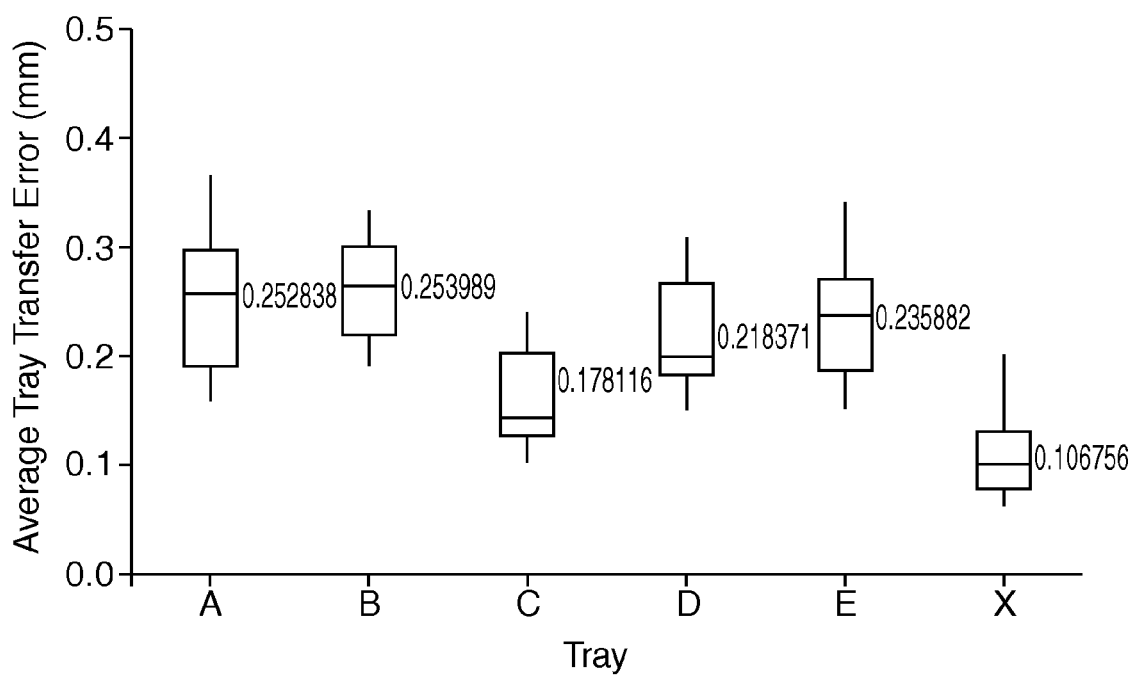
FIG. 21 is a graph showing positioning errors of appliances using an indirect bonding tray constructed in accordance with the present invention in comparison to other constructions of indirect bonding trays.

The results of the averaged transfer errors are set out in FIG. 21, and the numerical value associated with each box in FIG. 21 is an average of the values obtained for the three different arches. The data of FIG. 21 show that indirect bonding trays constructed according to the present invention exhibited the least amount of transfer error in comparison to the comparative indirect bonding trays. The averaged transfer error obtained using trays of the present invention was approximately 0.1 mm, while the averaged transfer errors obtained using the comparative indirect bonding trays ranged from approximately 0.18 mm to approximately 0.26 mm. In FIG. 21, the vertical lines corresponding to each average value represent the 0 to 100% range of obtained data, while the rectangles represent the 25 to 75% range of obtained data.

All patents and patent applications mentioned above are incorporated by reference herein. Additionally, a number of other variations to the invention described above are also possible. Consequently, the invention should not be deemed limited to the presently preferred embodiments as set out in detail above, but instead by a fair scope of the claims that follow along with their equivalents.

The invention claimed is:

1. An indirect bonding tray for orthodontic treatment comprising:
    a set of orthodontic appliances for a dental arch;
    a first matrix material extending over the appliances;
    a second matrix material extending over the first matrix material, wherein the second matrix material includes a portion having a surface with a configuration that matches the configuration of a portion of side tooth surfaces of the dental arch, and wherein the second matrix material exhibits a tensile stress at 20 percent elongation that exceeds the tensile stress at 20 percent elongation of the first matrix material; and
    an occlusal stop member connected to the second matrix material, the occlusal stop member including at least one section having a surface with a configuration that matches at least a portion of an occlusal tooth surface of the dental arch for contact with the dental arch, wherein the occlusal stop member has a Shore A hardness greater than the Shore A hardness of either the first or second matrix material.

2. An indirect bonding tray for orthodontic treatment according to claim 1 wherein the first matrix material includes a portion having a surface with a configuration that matches the configuration of a portion of side tooth surfaces.

3. An indirect bonding tray for orthodontic treatment according to claim 1 wherein the first matrix material surrounds each appliance.

4. An indirect bonding tray for orthodontic treatment according to claim 1 wherein the appliances have occlusal, facial and gingival sides, and wherein the first matrix material is in contact with the occlusal, facial and gingival sides of the appliances.

5. An indirect bonding tray for orthodontic treatment according to claim 1 wherein the second matrix material surrounds at least a portion of the occlusal stop member.

6. An indirect bonding tray for orthodontic treatment according to claim 1 wherein the second matrix material is connected to the occlusal stop member by a mechanical interlock.

7. An indirect bonding tray for orthodontic treatment according to claim 1 wherein the tray includes an external facial surface and wherein the second matrix material presents at least part of the external facial surface.

8. An indirect bonding tray for orthodontic treatment according to claim 1 wherein the tray includes an external lingual surface and wherein the second matrix material presents at least part of the external lingual surface.

9. An indirect bonding tray for orthodontic treatment according to claim 1 wherein the stop member comprises rapid prototyping material.

10. An indirect bonding tray for orthodontic treatment according to claim 1 wherein the first matrix material exhibits tensile stress in the range of about 62,000 Pascal to about 248,000 Pascal at 20 percent elongation.

11. An indirect bonding tray for orthodontic treatment according to claim 1 wherein the second matrix material exhibits tensile stress in the range of about $0.8 \times 10^6$ Pascal to about $3.3 \times 10^6$ Pascal at 20 percent elongation.

12. An indirect bonding tray for orthodontic treatment according to claim 1 wherein the first matrix material exhibits tensile stress in the range of about 112,000 Pascal to about 136,000 Pascal at 20 percent elongation.

13. An indirect bonding tray for orthodontic treatment according to claim 1 wherein the second matrix material exhibits tensile stress in the range of about $1.1 \times 10^6$ Pascal to about $1.4 \times 10^6$ Pascal at 20 percent elongation.

14. An indirect bonding tray for orthodontic treatment according to claim 1 wherein the second matrix material exhibits a tensile stress at 20 percent elongation that exceeds the tensile stress at 20 percent elongation of the first matrix material by a ratio in the range of about 5:1 to about 20:1.

15. An indirect bonding tray for orthodontic treatment according to claim 1 wherein the occlusal stop member includes a handle that extends in a facial direction past the second matrix material.

16. An indirect bonding tray for orthodontic treatment according to claim 1 wherein the occlusal stop member includes two posterior sections having at least one recess with a configuration that matches an occlusal tip of a molar tooth and at least one anterior section with at least one recess having a configuration that matches the configuration of an occlusal tip of an anterior tooth.

17. An indirect bonding tray for orthodontic treatment according to claim 16 wherein the occlusal stop member also includes a connecting section interconnecting each anterior section and each posterior sections, wherein the connecting section is more flexible than each anterior section and each posterior section.

18. An indirect bonding tray for orthodontic treatment according to claim 17 wherein the connecting section does not include a recess having a configuration that matches the configuration of an occlusal tip of a tooth.

19. An indirect bonding tray for orthodontic treatment according to claim 1 wherein the occlusal stop member is the only stop member of the tray that has a hardness that is greater than the hardness of the second matrix material.

* * * * *

UNITED STATES PATENT AND TRADEMARK OFFICE
CERTIFICATE OF CORRECTION

PATENT NO. : 7,845,938 B2
APPLICATION NO. : 11/689845
DATED : December 7, 2010
INVENTOR(S) : Kim et al.

It is certified that error appears in the above-identified patent and that said Letters Patent is hereby corrected as shown below:

First Page, Column 1
Line 1, Delete "Sungham" and insert -- Sunghan --, therefor.

Page 2, Column 1
Line 9, Below "7,168,950 B2 1/2007 Cinader, Jr. et al." insert -- 7,188,421 3/2007 Cleary et al. --.

Column 20
Line 16, Delete "MATERIAL"," and insert -- MATERIAL" [attorney docket 60546US002], --, therefor.

Column 23

Line 19, Delete " $P = T_{pedestal \rightarrow slot}^{-1} S$ " and insert -- $P = T_{pedestal \rightarrow slot}^{-1} S$ --, therefor.

Line 40-45, Delete "$\begin{bmatrix} a'_{11} & a'_{12} & a'_{13} & x'_o \\ a'_{21} & a'_{22} & a'_{23} & y'_o \\ a'_{31} & a'_{32} & a'_{33} & z'_o \\ 0 & 0 & 0 & 1 \end{bmatrix}_{base \rightarrow slot} \begin{bmatrix} a_{11} & a_{12} & a_{13} & x_o \\ a_{21} & a_{22} & a_{23} & y_o \\ a_{31} & a_{32} & a_{33} & z_o \\ 0 & 0 & 0 & 1 \end{bmatrix}_{pedestal \rightarrow slot} \begin{bmatrix} 0 \\ 0 \\ 0 \\ 1 \end{bmatrix}$" and insert -- $\begin{bmatrix} x_v \\ y_v \\ z_v \\ 1 \end{bmatrix} = \begin{bmatrix} a'_{11} & a'_{12} & a'_{13} & x'_o \\ a'_{21} & a'_{22} & a'_{23} & y'_o \\ a'_{31} & a'_{32} & a'_{33} & z'_o \\ 0 & 0 & 0 & 1 \end{bmatrix}_{base \rightarrow slot} \begin{bmatrix} a_{11} & a_{12} & a_{13} & x_o \\ a_{21} & a_{22} & a_{23} & y_o \\ a_{31} & a_{32} & a_{33} & z_o \\ 0 & 0 & 0 & 1 \end{bmatrix}_{pedestal \rightarrow base} \begin{bmatrix} 0 \\ 0 \\ 0 \\ 1 \end{bmatrix}$ --, therefor.

Signed and Sealed this
Twenty-sixth Day of April, 2011

David J. Kappos
*Director of the United States Patent and Trademark Office*

Column 26
Line 12, In Claim 1, delete "material." and insert -- material, wherein the first matrix material is spaced from the occlusal stop member. --, therefor.